United States Patent [19]

Muchowski et al.

[11] Patent Number: 4,548,951
[45] Date of Patent: Oct. 22, 1985

[54] HYPOTENSIVE BENZOXATHIOLE PYRROLIDINES

[75] Inventors: Joseph M. Muchowski, Sunnyvale; Jack Ackrell, Palo Alto, both of Calif.

[73] Assignee: Syntex (U.S.A.) Inc., Palo Alto, Calif.

[21] Appl. No.: 487,335

[22] Filed: Apr. 21, 1983

[51] Int. Cl.⁴ .................. C07D 411/06; A61K 31/39
[52] U.S. Cl. .................... 514/522; 548/526; 548/407; 549/32; 549/33; 549/31; 546/237
[58] Field of Search ............... 548/526, 407; 514/422

[56] References Cited

U.S. PATENT DOCUMENTS

| | | | |
|---|---|---|---|
| 3,436,403 | 4/1969 | Cornforth | 549/32 |
| 4,248,884 | 2/1981 | Legrand et al. | 424/274 OR |
| 4,342,692 | 8/1982 | Suh et al. | 548/526 X |

FOREIGN PATENT DOCUMENTS 2054581  2/1981  United Kingdom .

OTHER PUBLICATIONS

Tegeler et al., J. Heterocyclic Chem., 20 (1983), p. 867.

Primary Examiner—Donald G. Daus
Assistant Examiner—William A. Teoli, Jr.
Attorney, Agent, or Firm—Charles L. Hartman; Tom M. Moran; Alan M. Krubiner

[57] ABSTRACT

Compounds of the formula

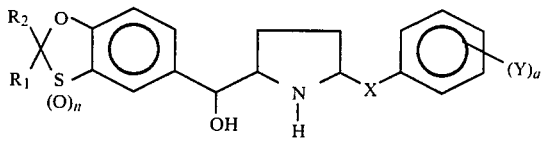

and the pharmaceutically acceptable, nontoxic, acid addition salts thereof, wherein $R_1$ and $R_2$ are each independently —H, lower alkyl, or cycloalkyl, with the proviso that $R_1$ and $R_2$ cannot both be —H or cycloalkyl at the same time;
$R_1$ and $R_2$ taken together are cycloalkyl of 4–7 carbons;
n is 0 or 1;
X is $(CH_2)_2$, CH=CH, or C≡C;
Y is independently selected from the group of —H, —Fl, —Br, —Cl, lower alkyl, and —$OR_3$; wherein $R_3$ is —H or lower alkyl; and
a is 1 or 2, or
two Y's taken together are —$OCH_2O$—;

are useful as regulators of the cardiovascular system, particularly as hypotensive agents.

24 Claims, No Drawings

HYPOTENSIVE BENZOXATHIOLE PYRROLIDINES

BACKGROUND OF THE INVENTION

1. Field of the Invention

This invention concerns benzoxathiole pyrrolidine compounds which affect the cardiovascular system and which are particularly effective as hypotensive agents. The invention is directed toward orally active, long lasting cardiovascular regulators of hypertension.

2. Related Disclosures

Compounds which most closely resemble, in molecular structure, the compounds of the present invention are useful in treating general disorders related to the cardiovascular system and other therapeutic applications.

Practolol and prenalterol which are amino-alcohol aryl ethers are well known and commercially available compounds which affect the $\beta_1$ adrenergic receptors of the peripheral system. *J. Med. Chem.*, 16:168 (1973).

In addition, there have been several deliberate attempts to combine $\beta_1$ affectors with vasodilators such as, for example, compounds which are naphthalenone phthalazinylhydrazones, and which may be hydrolyzed in the body to form hydralazine, a well known peripheral vasodilator, and bunolol, a general $\beta$ adrenergic blocker (see U.S. Pat. No. 4,061,636). In addition, sulfinalol (British Pat. No. 1,544,872) and its relatives are known antihypertensive/antiarrhythmic agents.

Cyclic compounds containing a 5 or 6 membered saturated nitrogen-containing ring, linked through a hydroxymethyl group to an aromatic nucleus, such as, for example, rimiterol (Pinder, R. M. et al, *Drugs*, 14:81 (1977)) and other compounds disclosed in European Pat. No. 10460, Belgium Pat. No. 884176 and U.S. Pat. No. 4,342,692 have known physiological activities and are psychotropic, cardiotonic, antihypertensive, antiallergic, and hypolipaemic agents. Rimiterol, itself, is a known $\beta_2$ agonist. Some of these hypotensive compounds have recently been described in European Pat. No. 22408.

British Pat. No. 1,392,674 also discloses, as agents for treatment of acutely depressed cardiac contractility, compounds related in structure to those of the invention herein.

SUMMARY OF THE INVENTION

One aspect of this invention relates to compounds of the formula

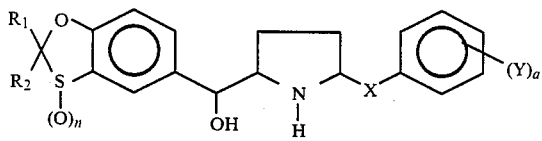

and the pharmaceutically acceptable, nontoxic, acid addition salts thereof, wherein $R_1$ and $R_2$ are each independently —H, lower alkyl, or cycloalkyl, with the proviso that $R_1$ and $R_2$ cannot both be —H or cycloalkyl at the same time;

$R_1$ and $R_2$ taken together are cycloalkyl of 4–7 carbons;

n is 0 or 1;

X is $(CH_2)_2$, CH=CH, or C≡C;

Y is independently selected from the group of —H, —Fl, —Br, —Cl, lower alkyl, and —OR$_3$; wherein $R_3$ is —H or lower alkyl; and a is 1 or 2, or two Y's taken together are —OCH$_2$O—;

which are useful as regulators of the cardiovascular system, particularly as hypotensive agents.

Another aspect of this invention concerns the method of regulating the cardiovascular system in mammals by administering to a mammal in need of such treatment a therapeutically effective amount of a compound of this invention or their pharmaceutically acceptable salts.

Still another aspect of the invention is a pharmaceutical composition containing a suitable pharmaceutical excipient and a compound of this invention, or pharmaceutically acceptable salt thereof.

Finally, in yet another aspect, this invention concerns processes for the preparation of the compounds of this invention and their salts.

DETAILED DESCRIPTION OF THE INVENTION

Definitions

As used herein:

"Pharmaceutically acceptable, nontoxic, acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Lower alkyl" means a branched or unbranched saturated hydrocarbon chain of 1–6 carbons, such as, for example, methyl, ethyl, n-propyl, isopropyl, n-butyl, isobutyl, t-butyl, n-pentyl, iso-pentyl, t-pentyl, hexyl, iso-hexyl and the like.

"Cycloalkyl" means cyclic saturated monocyclic hydrocarbon chain of 4–7 carbons, such as cyclobutyl, cyclopentyl, cyclohexyl and cycloheptyl.

The compounds of the invention herein have at least three chiral centers. Chiral centers are the 2- and 5-positions of the pyrrolidine ring at which the side chains are substituted and the chain position where the hydroxy group is attached. Additional centers of asymmetry are introduced when $R_1$ and $R_2$ are not equivalent and/or when n is 1.

Embodiments wherein both 2- and 5-ring hydrogens are on the same side of the plane of the pyrrolidine ring are designated "cis"; those wherein they are on opposite sides are "trans."

"Erythro/threo" terminology is used to designate the relationship between the configurations of the group attached to the carbon atom bearing the hydroxyl substituent and of the carbon atom 5 of the pyrrolidine ring. "Erythro" indicates those embodiments wherein the hydrogen of carbon atom 5 of the ring and the hydrogen of the hydroxylated carbon occupy the same side of the molecule.

"Threo" indicates those embodiments wherein the hydrogen of carbon atom 5 of the ring and the hydrogen of the hydroxylated carbon are on the opposite sides of the molecule. For numbering system see below.

The IUPAC nomenclature and numbering system are used. The numbering system for pyrrolidine and phenyl rings is shown in the scheme illustration and is used in naming the intermediates and product compounds of the invention.

Exemplary names are given in the following Preferred Embodiment Section.

PRESENTLY PREFERRED EMBODIMENTS

Presently preferred embodiments of this invention are the following groups.

One preferred group of the compound are those wherein $R_1$ and $R_2$ are each independently —H, lower alkyl, or cycloalkyl, with the proviso that $R_1$ and $R_2$ cannot both be —H or cycloalkyl at the same time;

$R_1$ and $R_2$ taken together are cycloalkyl of 4–7 carbons;

n is 0 or 1;

X is $(CH_2)_2$, CH=CH or C≡C;

Y is independently selected from the group of —H, —Fl, —Br, —Cl, lower alkyl, and —OR$_3$; wherein $R_3$ is —H or lower alkyl; and a is 1 or 2, or two Y's taken together are —OCH$_2$O—.

One more preferred group of compounds are those wherein $R_1$ and $R_2$ are each lower alkyl, or one is lower alkyl and the other is cycloalkyl, or taken together $R_1$ and $R_2$ are cycloalkyl, n is 0, X is CH=CH, Y is as defined above, and a is 1 or 2. A particularly preferred compound of this group and a representative is ±cis erythro 2-(phenethenyl)-5-(2,2-dimethyl-1,3-benzoxathiol-5-yl)hydroxymethylpyrrolidine.

Yet a more preferred group of compounds are those wherein $R_1$ and $R_2$ taken together are cycloalkyl, n is 0, X is $(CH_2)_2$, Y is as defined above but preferably methoxy, and a is 1 or 2. A representative compound and particularly preferred in this group is ±cis erythro 2-(p-methoxyphenethyl)-5-(2,2-spirocyclopentane-1,3-benzoxathiol-5-yl)hydroxymethylpyrrolidine.

Most preferred group of compounds are those where $R_1$ and $R_2$ are lower alkyl, n is 0, X is $(CH_2)_2$, Y is as defined above and a is 1 or 2. A representative compound and most preferred is ±cis erythro 2-(p-methoxyphenethyl)-5-(2,2-dimethyl-1,3-benzoxathiol-5-yl)hydroxymethylpyrrolidine.

In all cases both the free base forms and the pharmaceutically acceptable salts are included in the description.

PREPARATION PROCEDURES

The compounds of this invention can be prepared either according to Reaction Scheme 1, 2 or 3.

In all Reaction Schemes, designations $R_1$, $R_2$, Y, X, a, and n are the same as previously defined in the Summary.

Reaction Scheme 1 illustrates the preparation of 5-formamidoacetyl-2,2-substituted-1,3-benzoxathioles.

Reaction Scheme 2 illustrates the preparation of N-methylpiperidinium iodide wherein X is CH=CH (Steps 10 and 12), X is CH$_2$—CH$_2$ (Steps 10,11 and 13) or X is C C (Steps 14–15).

Reaction Scheme 3 illustrates the preparation of ±cis erythro-2-substituted phenethyl-5-(2,2 substituted-1,3-benzoxathiol-5-yl)hydroxymethylpyrrolidine.

REACTION SCHEME 1
-continued

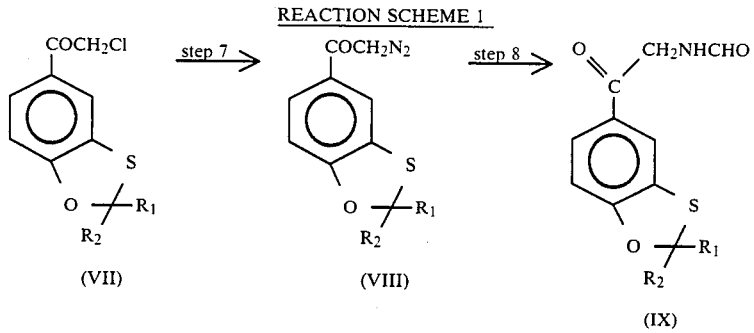

Reaction Scheme 1 describes the preparation of the intermediate 5-formamidoacetyl-2,2-dialkyl-1,3-benzoxathioles (IX) by following reaction steps 1–8.

Compound I is mixed, in approximately 1:10 amounts (w/w), with halogenated sulfonic acid, preferably chlorosulfonic acid. The mixture is reacted for 12–26 hours, preferably about 18 hours, and then quenched by pouring on crushed ice. The precipitate is filtered and dissolved in a suitable ester such as, for example, ethyl acetate, propyl acetate, ethyl propionate, preferably ethyl acetate. The solution is washed with brine, dried and evaporated to give chlorosulfonated compound II. (Step 1)

Compound II is dissolved in a hot aliphatic carboxylic acid, such as formic acid, propionic acid, butyric acid and the like, preferably acetic acid, and a reducing agent, preferably zinc powder, is added. The mixture is refluxed for 4–10 hours, preferably 6 hours, cooled and filtered to remove the insoluble zinc salts. The filtrate is evaporated and the residue is stirred with excess of dilute inorganic acid, preferably 3 M hydrochloric acid, the precipitate is filtered and dried to yield the mercapto compound III. (Step 2)

Step 3 illustrates the preparation of various 5-carboxy-2,2-substituted 1,3 benzoxathioles. Various $R_1$ and $R_2$ substitution is achieved by utilizing appropriately substituted aliphatic ketone in the following procedure. For details see Preparation 3.

Compound III is dissolved in an aromatic hydrocarbon such as, for example, benzene, xylene, ethylbenzene, and an aliphatic ketone, such as acetone, butanone, cyclopentanone or cyclohexanone is added. Then, a quantity of a catalyst-dehydrating agent, preferably boron trifluoride etherate is added and the mixture is reacted for 2–8 hours, preferably 4 hours. The organic layer is removed and evaporated and the residue recrystallized from alcohol, such as ethanol, propanol or butanol, preferably methanol, to yield 2,2-substituted benzoxathiole compound IV. (Step 3)

Compound IV is reacted with, for example, oxalyl chloride, thionyl chloride, phosphorous pentachloride in a suitable solvent such as di-propylether, tetrahydrofuran, dioxane, preferably diethyl ether at room temperature to reflux (25° to 100°) 0.5–6 hours, preferably 2 hours. The resulting mixture is cooled, and the solvent evaporated to give a compound represented by formula V. (Step 4) Compound V is added to a solution of diazomethane in ether, preferably ethyl ether, and reacted under constant stirring for 5–60 hours, preferably 18 hours, at 10°–30° C., preferably ambient temperature, to give compound VI. (Step 5) The solution of compound VI is then reacted with methanolic hydrogen chloride, to afford, after appropriate purification, the compound VII. (Step 6)

A solution of compound VII in a dipolar aprotic solvent such as dimethylformamide, dimethylsulfoxide, dimethyl sulfone and the like, preferably acetonitrile, is reacted for from 1 hour to 3 days, preferably 2 days, with a metal azide, preferably sodium azide. After isolation, the product is crystallized from an alcohol, preferably methanol, to yield compound VIII. (Step 7)

Compound VIII is mixed with a reducing agent, preferably stannous chloride, and a carboxylic acid salt, preferably sodium formate, in a mixture of acid anhydride(s) and saturated aliphatic carboxylic acid, preferably in the mixture of acetic-formic anhydride and formic acid. The mixture is reacted for 10–60 hours, preferably 24 hours, at 10°–30° C., preferably at room temperature, quenched with ice and inorganic acid, preferably dilute hydrochloride acid, and extracted with an organic solvent, preferably ethyl acetate, dried and purified using methods well-known in the art, yielding compound IX. (Step 8)

REACTION SCHEME 2

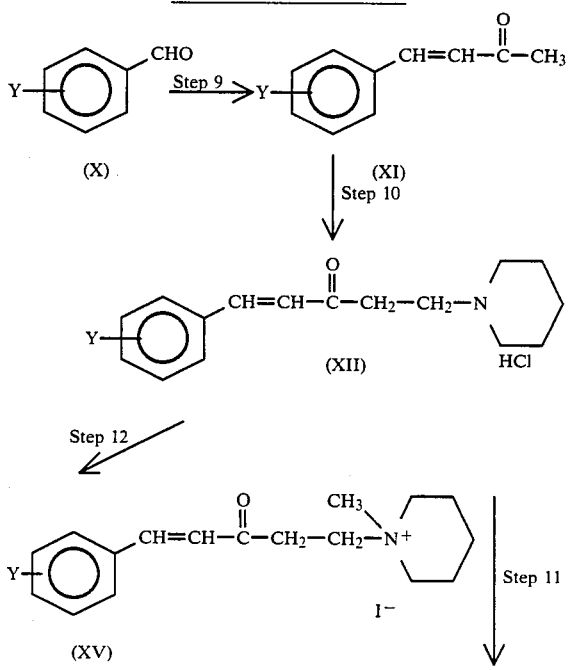

-continued
REACTION SCHEME 2

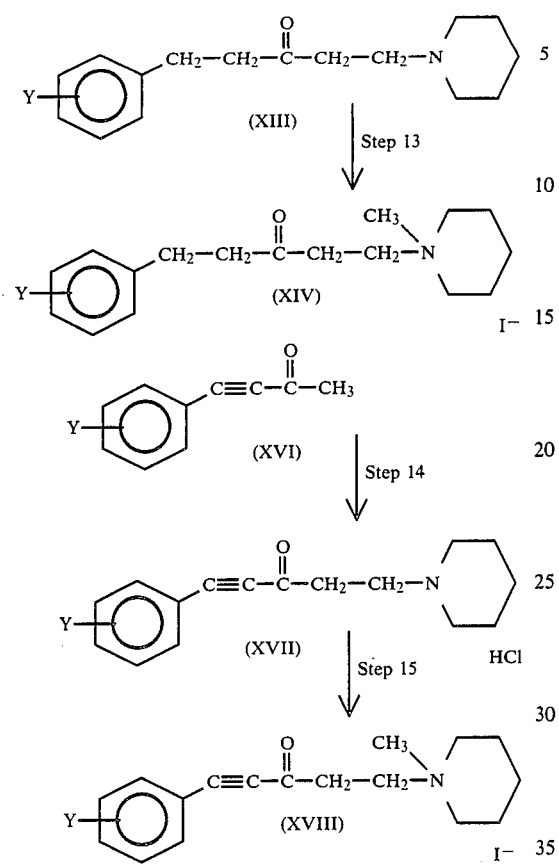

Reaction Scheme 2 describes the preparation of the intermediate N-methylpiperidinium iodides.

The substituted aldehyde (X), see Preparation 7.D., is mixed with acetone and is treated with an aqueous solution of an alkali metal hydroxide, preferably sodium hydroxide. After one to 12 hours, preferably 3 hours, the reaction mixture is neutralized by the addition of acetic acid and evaporated. The residue is washed with water, dried and crystallized from methanol to give the substituted benzalacetone (XI). (Step 9)

The substituted benzalacetone (XI) is dissolved in an alcohol such as methanol, ethanol and the like and treated with piperidine hydrochloride and paraformaldehyde and heated under reflux for 1 to 10, preferably 4 hours. The solution is cooled and the product filtered to yield the substituted piperidinium hydrochloric salts (XIII). (Step 10)

A solution of (XII) in water is stirred and an alkali metal base such as sodium hydroxide, potassium hyrdoxide, sodium carbonate, preferably potassium carbonate, is added. The mixture is extracted with ethyl acetate and the extract is dried with potassium carbonate and filtered. The filtrated is stirred with a palladium on carbon catalyst in a hydrogen atmosphere until hydrogen uptake ceases. The reaction mixture is filtered to yield a solution of amine (XIII) (Step 11) which is cooled in ice and treated with excess methyl iodide. After 8 to 24 hours, preferably 16 hours the precipitate is collected by filtration and dried. In this way there is obtained the N-methylpiperidinium salt wherein X is $CH_2-CH_2$ (XIV). (Step 13)

The intermediate alkenyl-N-methylpiperidinium salt wherein X is CH=CH (XV) are prepared directly from intermediate (XII) by dissolving compound (XII) in water and adding an excess of alkali metal base such as sodium hydroxide, potassium hydroxide, sodium carbonate, preferably potassium carbonate. The reaction mixture is extracted with ethyl acetate and the extract dried with potassium carbonate. The reaction mixture is filtered and the filtrate added to an excess of methyl iodide. After 8 to 24 hours, preferably 12 hours the precipitate is collected by filtration and dried. In this way there is obtained the alkenyl-N-methylpiperidinium salts (XV). (Step 12)

The intermediate alkynyl-N-methylpiperidinium salts wherein X is C≡C (XVIII) are prepared starting from compound (XVI) commercially available from, for example, Aldrich, and utilizing procedures essentially identical as those described above for the conversion of compound (XI) to compound (XII), (Step 10) and conversion of compound (XII) to compound (XV) (Step 12) but herein illustrated by Steps 14 and 15.

REACTION SCHEME 3

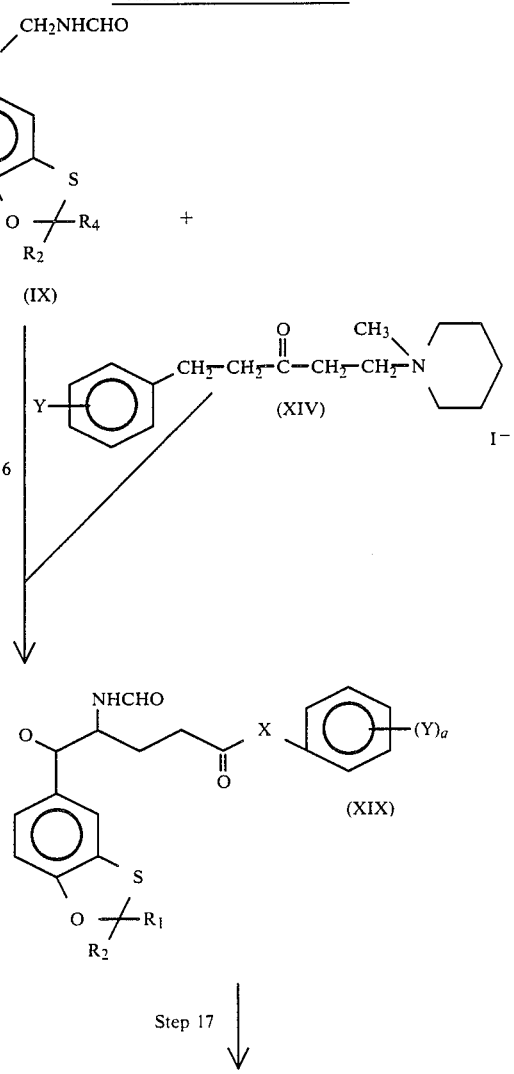

-continued
REACTION SCHEME 3

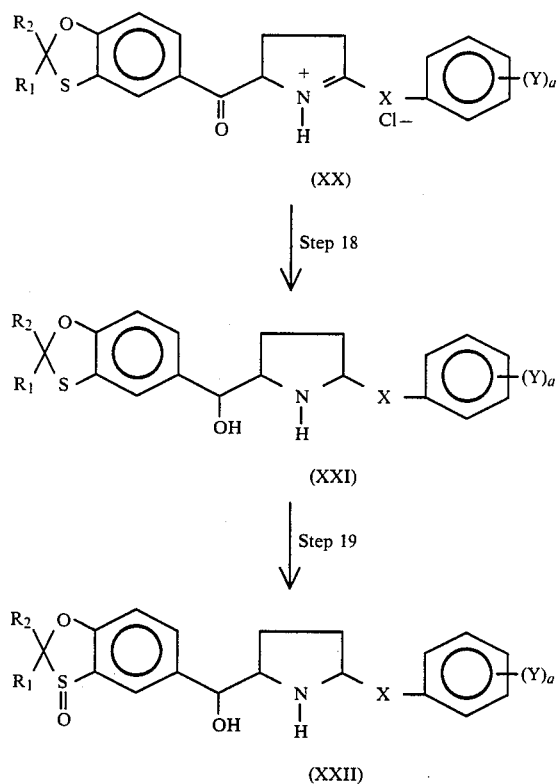

Reaction Scheme 3 describes the preparation of the 2,5 disubstituted pyrrolidines (XXI) and (XXII).

Compound IX is dissolved in a dipolar aprotic solvent, such as formamide, dimethyl acetamide, dimethyl sulfoxide and the like, preferably dimethylformamide and mixed with appropriately substituted N-methyl piperidinium salt (XIV),(XV), or (XVIII). An alkali metal carbonate, preferably potassium carbonate is added and the mixture is stirred from 1 to 24 hours, preferably 4 hours. The reaction mixture is quenched with water and inorganic acid, preferably dilute hydrochloric acid, and extracted with organic solvent, preferably ethyl acetate, dried and purified to yield compound (IXX) (Step 16).

Compound (XIX) is cyclized by dissolving it in a polar solvent such as, for example, methanol, ethanol, dimethoxyethane, preferably methanol, and treated with concentrated acid such as hydrochloric, sulfuric or nitric acid, preferably hydrochloric acid. The cyclization proceeds for 8-72 hours, preferably 24 hours, at a temperature of about 8°-40° C., preferably at ambient temperature to afford compound (XX). The resulting compound of formula (XX) is dissolved in an aprotic solvent, preferably methanol, cooled to −30° C. to −50° C., preferably to −40° C., and treated with chemical reducing agent such as, for example, lithium aluminum hydride or lithium aluminum borohydride, or other alkali metal, preferably sodium borohydride, to reduce a keto group to a hydroxy and solvent is evaporated. The residue is treated with ammonium chloride solution and extracted with ethyl acetate. The organic layer is separated, washed, dried, and evaporated to yield a residue which is dissolved in an aprotic solvent, preferably methanol and the solution is acidified by the addition of hydrogen chloride in alcohol, preferably methanol, to yield compound (XXI) (Steps 17 and 18).

The compound (XXI) can be subsequently oxidized to afford the sulfinyl compound (XXII) by treatment with a peroxocarboxylic acid, for example, peracetic, perbromic, n chloroperbenzoic acid and the like for 5-120 minutes, preferably 15 minutes. The mixture is evaporated and the residue is triturated with ethyl acetate and the insoluble material filtered off and recrystallized from an alcohol preferably ethanol to give compound (XXII) (Step 19).

The preparation of compounds of type (XXI) and (XXII) where X is CH=CH or X is C≡C is carried out in essentially the same manner as for the saturated compounds wherein X is $CH_2$—$CH_2$ except that N-methylpiperidinium salts (XV) leading to (XXI) and (XXII), where X is CH=CH; and (XVIII) leading to (XXI) and (XXII) where X is C≡C are substituted for (XIV).

In summary, a compound of the formula

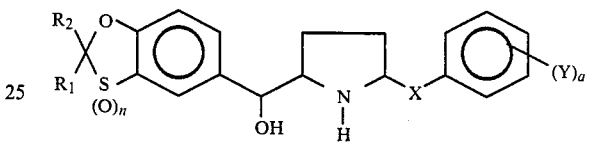

and the pharmaceutically acceptable, nontoxic, acid addition salts thereof, wherein $R_1$ and $R_2$ are each independently —H, lower alkyl, or cycloalkyl, with the proviso that $R_1$ and $R_2$ cannot both be —H or cycloalkyl at the same time;

$R_1$ and $R_2$ taken together are cycloalkyl of 4-7 carbons;

n is 0 or 1;

X is $(CH_2)_2$, CH=CH, or C≡C;

Y is independently selected from the group of —H, —Fl, —Br, —Cl, lower alkyl, and —$OR_3$; wherein $R_3$ is —H or lower alkyl; and a is 1 or 2, or two Y's taken together are —$OCH_2O$—;

is prepared by the process which comprises and:

(a) reducing a compound of the formula

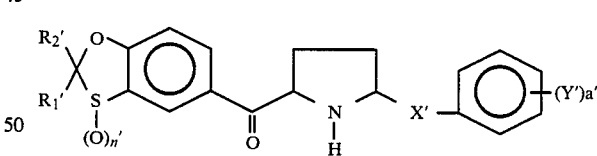

wherein $R_1'$, $R_2'$, $R_3'$, n', X', Y' and a' are as $R_1$, $R_2$, $R_3$, n, X, b, Y, and a, respectively, and are as defined hereinabove;

(b) converting the free base of the compound to a pharmaceutically acceptable acid addition salt;

(c) converting a salt of the compound to a free base;

(d) converting a salt of the compound to another salt.

All compounds may be prepared in either cis or trans form, or as erythro or threo compounds and still other centers of asymmetry may be introduced where $R_1$ and $R_2$ in compound (IX) are not equivalent, or where the compound is sulfinyl S(O).

Accordingly, all compounds described above may be prepared as any of these stereochemically pure forms, as racemic mixtures or as a mixture of some or all of the diastereomeric forms. The invention is intended to encompass all of these possibilities and, unless otherwise specified, the compounds of this invention are prepared as either racemic mixtures or mixtures of diastereomers. It should be understood that the claims appended to this specification are meant to include all of the aforementioned possibilities, whether in stereochemically pure form as an optically active stereoisomer or as a mixture of any of the isomers.

Separation of diastereomers can, of course, be carried out by any standard separation techniques, such as thin layer, thick layer or high pressure liquid chromatography, or by fractional crystallization. Each racemic diastereomer (or enantiomeric pair) may, if desired, be resolved into its optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-$\pi$-sulfonic acid, camphoric acid, methoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of this invention.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the Preparations and Examples hereinbelow. However, other equivalent separation or isolation procedures could, of course, also be used.

Compounds which are prepared as free base can be converted to various salts. Salts can be reconverted back to the free base, or one salt can be exchanged for other salt by methods and means known in the art and are illustrated in Examples 6–8.

The salt products are also isolated by conventional means. For example, the reaction mixtures may be evaporated to a dryness, and the salts can be further purified by conventional methods.

UTILITY AND ADMINISTRATION

Utility

The compounds of the invention are inotropic agents and therefore useful as cardiovascular regulators particularly as hypotensive agents. When administered orally or subcutaneously, they relieve hypertension in spontaneously hypertensive rats (SHR) and affect rate and force of the heart beat. Accordingly, they are potentially useful as drugs for management of hypertension. They are also active as bronchodilators.

Administration

Administration of the active compounds and salts described herein can be via any of the accepted modes of administration for cardiovascular system regulating agents. These methods include oral or parenteral routes of administration. Parenteral modes of administration are such as intravenous, subcutaneous, intradermal, or intramuscular injections. However, oral mode of administration is preferred. Parenteral route of administration is the administration of drugs to a patient by injection under or through one or more layers of the skin or mucous membrane. Parenteral administration would preferably be reserved for crisis situations, wherein the subject is unable to swallow or administer the medication to himself.

The amount of active ingredient administered will, of course, be dependent on the subject being treated, on the severity of the affliction, on the manner of administration and on the judgment of the prescribing physician. However, an effective dosage is in the range of 0.001–50 mg/kg/day, preferably 0.01–1 mg/kg/day. For an average 70 kg human, this would amount to 0.07–3500 mg per day, preferably 0.7–70 mg/day.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.1%–95% active ingredient, preferably 1%–70%.

For parenteral administration, such as, for example, intravenous injections, the compound is dissolved in a vehicle. Vehicle may be, for example, aqueous vehicle, such as sodium chloride injection, Ringer's injection, dextrose injection and others, water miscible vehicle, such as ethyl alcohol, polyethylene glycol of the liquid series or propylene glycol, or nonaqueous vehicles such a corn oil, peanut oil or sesame oil. Vehicle will be buffered to the proper pH in order to stabilize a solution against chemical degradation and formed in such a way as to control isotonicity of injection. Other substances may also be added as antimicrobial or antioxidant agents.

For use as bronchodilators, administration of the active compounds and salts described herein can be via any of the accepted modes for bronchodilation, i.e., any mode described above can be used and compounds may also be administered in aerosol form.

Pharmaceutical Composition

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient, a compound of this invention or the pharmaceutically acceptable salts as an active ingredient thereof. In addition, it may include other medicinal or pharmaceutical agents, carriers, adjuvants, etc.

The composition or formulation to be administered will, in any event, contain a quantity of the active ingredient(s) in an amount effective to alleviate the symptoms of the subject being treated.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like. The active ingredient as defined above may be formulated as suppositories using as the carrier, for example, polyalkylene glycols, such as propylene glycol.

Liquid pharmaceutically administerable compositions can be prepared by dissolving or dispersing, or otherwise preparing an active ingredient (as defined above), and mixing it optionally with a pharmaceutical adjuvant in a carrier, such as, for example, water, saline, aqueous dextrose, glycerol, ethanol, and the like, to thereby form a solution or suspension.

If desired, the pharmaceutical composition to be administered may also contain minor amounts of nontoxic auxiliary substances such as wetting or emulsifying agents, pH buffering agents and the like, such as for example, sodium acetate, sorbitan monolaurate, triethanolamine sodium acetate, sorbitan monolaurate, triethanolamine oleate, etc.

Methods of preparing various pharmaceutical compositions with certain amount of active ingredient are known, or will be apparent, to those skilled in this art. For examples, see *Remington's Pharmaceutical Sciences*, Mack Publishing Company, Easton, Pa., 15th Edition (1975).

PREPARATIONS AND EXAMPLES

The following Preparations and Examples serve to illustrate the invention. They should not be construed as narrowing or limiting its scope.

Roman numerals in parentheses refer to structures in Reaction Schemes.

Preparations illustrate the process of making starting materials (I)–(XVIII). Specifically, Preparations 1–11 illustrate how to prepare compounds (I)–(IXX) wherein $R_1$ and $R_2$ are each the same or different and may be hydrogen, lower alkyl or cycloalkyl with proviso that no both $R_1$ and $R_2$ are at the same time hydrogens or cycloalkyls, but taken together $R_1$ and $R_2$ may be cycloalkyl. Preparations 12–18 illustrate the preparation of compounds (I)–(IXX) wherein $R_1$ and $R_2$ taken together are cycloalkyl of 4–7 carbons. Examples illustrate cyclization of compound (IXX) and preparation of compounds (XXI) and (XXII).

PREPARATION 1

Preparation of 3-Chlorosulfonyl-4-Hydroxybenzoic Acid (II)

55 g of p-Hydroxybenzoic acid (I) (Aldrich) was added in small portions to 545 g of chlorosulfonic acid (Aldrich) while stirring at room temperature. After 18 hours the reaction mixture was poured in a thin stream upon crushed ice (5 liters). The product was filtered and the precipitate dissolved in ethyl acetate. The solution was then washed with brine, dried with magnesium sulfate, filtered and evaporated to yield 65 g of 3-chlorosulfonyl-4-hydroxybenzoic acid (II), m.p. 181°–182° C.

PREPARATION 2

Preparation of 3-Mercapto-4-Hydroxybenzoic acid (III)

70 g of 3-chlorosulfonyl-4-hydroxybenzoic acid (II), dissolved in 200 ml of hot acetic acid, was treated with 70 g of zinc powder added in small portions to maintain gentle reflux. After refluxing for a further 6 hours the reaction mixture was cooled and the insoluble zinc salts collected by filtration. The filtrate was evaporated and the residue dissolved in 3 M dilute hydrochloric acid. The insoluble zinc salts isolated in the original filtration were also dissolved in 3 M hydrochloric acid and the combined solutions were extracted three times with ethyl acetate. The extracts were combined, washed with brine, dried over $MgSO_4$ and evaporated to yield about 30 g of 3-mercapto-4-hydroxybenzoic acid (III), m.p. 138°–141° C.

PREPARATION 3

A. Preparation of 5-Carboxy-2,2-Dimethyl-1,3-Benzoxathiole (IV)

16 g of 3-mercapto-4-hydroxybenzoic acid (III) was dissolved in a mixture of 300 ml of toluene and 50 ml of acetone. 50 ml of boron trifluoride etherate was added and the mixture was stirred at room temperature for 4 hours. Ice (50 g) was added and the mixture was stirred for a further 1 hour. The organic layer was separated, washed with brine, dried with magnesium sulfate and evaporated to leave a solid residue. The residue was recrystallized from aqueous methanol to yield 15 g of 5-carboxy-2,2-dimethyl-1,3-benzoxathiole (IV), m.p. 124°–125° C.

B. Preparation of Various 5-Carboxy-2,2-Substituted-1,3-Benzoxathioles

Similarly, various other 2,2-substituted 1,3-benzoxathioles can be prepared by substituting acetone with various ketones, such as diethyl ketone, dipropyl ketone, di-isopropyl ketone, di n-butyl ketone, di-isobutyl ketone, ethyl methyl ketone, methyl propyl ketone, butyl methyl ketone, ethyl propyl ketone, butyl ethyl ketone, butyl propyl ketone, methyl pentyl ketone, hexyl methyl ketone, cyclopropyl methyl ketone, cyclobutyl methyl ketone, cyclopentyl methyl ketone, cyclohexyl methyl ketone, or others, to obtain the following compounds:

5-carboxy-2,2-diethyl-1,3-benzoxathiole;
5-carboxy-2,2-di-n-propyl-1,3-benzoxathiole;
5-carboxy-2,2-di-isopropyl-1,3-benzoxathiole;
5-carboxy-2,2-di-n-butyl-1,3-benzoxathiole;
5-carboxy-2,2-di-isobutyl-1,3-benzoxathiole;
5-carboxy-2-methyl-2-propyl-1,3-benzoxathiole;
5-carboxy-2-butyl-2-methyl-1,3-benzoxathiole;
5-carboxy-2-ethyl-2-propyl-1,3-benzoxathiole;
5-carboxy-2-butyl-2-ethyl-1,3-benzoxathiole;
5-carboxy-2-butyl-2-propyl-1,3-benzoxathiole;
5-carboxy-2-methyl-2-pentyl-1,3-benzoxathiole;
5-carboxy-2-hexyl-2-methyl-1,3-benzoxathiole;
5-carboxy-2-cyclopropyl-2-methyl-1,3-benzoxathiole;
5-carboxy-2-cyclobutyl-2-methyl-1,3-benzoxathiole;
5-carboxy-2-cyclopentyl-2-methyl-1,3-benzoxathiole;
5-carboxy-2-cyclohexyl-2-methyl-1,3-benzoxathiole;
and others.

PREPARATION 4

A. Preparation of 5-Chloroacetyl-2,2-Dimethyl-1,3-Benzoxathiole (VII)

A mixture consisting of 10 g of 5-carboxy-2,2-dimethyl-1,3-benzoxathiole (IV), 10 g of oxalyl chloride and 20 ml of ether was boiled gently for 2 hours. The solution was cooled and evaporated and the residue (V) was added to an ether solution of diazomethane prepared from 25 g of N-nitroso-N-methyl urea. After stirring the mixture for 18 hours at room temperature the solution (VI) was acidified with methanolic hydrogen chloride and then evaporated to leave a solid residue which was recrystallized from ether/hexane to yield 6 g of 5-chloroacetyl-2,2-dimethyl-1,3-benzoxathiole (VII), m.p. 84°–86° C.

B. Preparation of Other 5-Chloroacetyl-2,2-Substituted-1,3-Benzoxathioles

The same procedure as described in Part A of this preparation is used to prepare other 5-chloroacetyl-2,2-substituted-1,3-benzoxathioles by substituting 5-carboxy-2,2-dimethyl-1,3-benzoxathiole with compounds prepared in Preparation 3.B.

PREPARATION 5

A. Preparation of 5-Azidoacetyl-2,2-Dimethyl-1,3-Benzoxathiole (VIII)

A solution of 20 g of 5-chloroacetyl-2,2-dimethyl-1,3-benzoxathiole (VII) in acetonitrile (100 ml) was stirred for two days with 7 g of finely powdered sodium azide. The reaction mixture was filtered, evaporated and the residue recrystallized from methanol to yield 12 g of 5-azidoacetyl-2,2-dimethyl-1,3-benzoxathiole (VIII), m.p. 52°–53° C.

B. Preparation of Other 5-Azidoacetyl-2,2-Substituted-1,3-Benzoxathioles

To prepare other 5-azidoacetyl-2,2-substituted-1,3-benzoxathioles, the same procedure as described in Part A of this preparation is used substituting 5-chloroacetyl-2,2-dimethyl-1,3-benzoxathiole with compounds prepared in Preparation 4.B.

PREPARATION 6

A. Preparation of 5-Formamidoacetyl-2,2-Dimethyl-1,3-Benzoxathiole (IX)

10 g of 5-azidoacetyl-2,2-dimethyl-1,3-benzoxathiole (VIII) was added portionwise to a cooled solution of 20 g stannous chloride and 7 g sodium formate in the mixture of 16 ml of acetic-formic anhydride and 9 ml of formic acid. After 14 hours at room temperature the mixture was quenched with ice and dilute hydrochloric acid and extracted with ethyl acetate. The extract was dried over MgSO$_4$, evaporated, and the residue purified by chromatography through a column of silica gel eluted with ethyl acetate-hexane (1:1) to yield 6 g of 5-formamidoacetyl-2,2-dimethyl-1,3-benzoxathiole (IX) as a yellow oil.

| n.m.r. | 1.85 ppm (6 H; 2 × CH$_3$ |
| --- | --- |
|  | 4.8 ppm (2H; CH$_2$) |
|  | 6.7–7.8 ppm (2H; Ar—H) |
| mass spec. | 440 (m$^+$—H |

B. Preparation of Other 5-Formamidoacetyl-2,2-Substituted-1,3-Benzoxathioles To prepare other 5-formamidoacetyl-2,2-substituted-1,3-benzoxathioles, the same procedure as described in Part A of this preparation is used substituting 5-azidoacetyl-2,2-dimethyl-1,3-benzoxathiole with compounds prepared in Preparation 5.B.

PREPARATION 7

Preparation of N-[3-Oxo-5-(3,4-Methylenedioxy)Phenyl]Pentyl-N-Methylpiperidinium Iodide

A. Preparation of Piperonalacetone (XI)

(Y is 3,4—OCH$_2$—O)

A solution of 100 g piperonal in 900 ml acetone was stirred at room temperature with 15 ml of 10% aqueous sodium hydroxide and 30 ml of water. After 3 hours 5 ml of acetic acid was added and the reaction mixture was evaporated. The residue was recrystallized from methanol and dried in vacuo to yield 60 g of piperonalacetone, m.p. 104°–105° C. (EtoAc).

B. Preparation of Nn-[3-oxo-5(3,4-Methylenedioxy)Phenyl]Pent-4-enyl-piperidinium Hydrochloride (XII)

(Y is 3,4—OCH$_2$—O)

A solution of 45 g piperidine in ethanol was converted into the hydrochloride salt by the addition of a solution of hydrogen chloride in methanol (25% w/v). To this solution was added 90 g of piperonalacetone followed by 20 g of paraformaldehyde. The reaction mixture was refluxed 24 hours then a further 15 g of paraformaldehyde was added and the mixture refluxed for a further 15 hours. The solution was cooled, the product filtered and washed with acetonitrile to yield 55 g of 5(3,4-methylenedioxy)phenyl-3-oxo-pent-4-enyl-piperidinium hydrochloride, m.p. 188° C.

C. Preparation of N-[3-Oxo-5(3,4-Methylenedioxy)Phenyl]Pentyl-N-Methylpiperidinium Iodide (XIV)

(Y is 3,4—OCH$_2$—O)

50 g of 5(3,4-methylenedioxy)phenyl-3-oxo-pent-4-enylpiperidinium hydrochloride was stirred with 100 ml of 10% aqueous sodium hydroxide and 100 ml of ether. After 1 hour the ether layer was separated, dried with potassium carbonate, filtered and evaporated to leave the free base as a pale yellow oil. The oil was taken up in ethyl acetate and hydrogenated over a poisoned Engelhardt catalyst (5% Pd on carbon) at 50 psi, until hydrogen uptake ceased. The colorless solution was filtered and slowly added to a solution of 75 ml of methyl iodide in 100 ml of ethyl acetate and cooled in ice. The reaction mixture was allowed to warm to room temperature for 18 hours, then filtered to yield 55 g of N-[3-oxo-5(3,4 methylenedioxy)phenyl]pentyl-N-methyl-yl-piperidinium iodide as a white solid, m.p. 105°–107° C.

D. Preparation of Other N-Methylpiperidinium Iodides

Similarly, other N-methylpiperidinium iodides can be prepared by following the procedure of Preparation 7.A., B., and C., but substituting piperonal with variously substituted benzaldehydes such as:

benzaldehyde; p-fluorobenzaldehyde; o-fluorobenzaldehyde; p-bromobenzaldehyde; o-bromobenzaldehyde; p-chlorobenzaldehyde; p-methylbenzaldehyde; 3,4-dimethylbenzaldehyde; p-ethylbenzaldehyde; 2,6-diethylbenzaldehyde; p-butylbenzaldehyde; p-hexylbenzaldehyde; p-ethoxybenzaldehyde; 3,4-diethoxybenzaldehyde; p-methoxybenzaldehyde (anisaldehyde), and others;

to obtain:

N(3-oxo-5-phenyl)pentyl-N-methylpiperidinium iodide;
N(3-oxo-5-p-fluorophenyl)pentyl-N-methyl-piperidinium iodide;
N(3-oxo-5-o-fluorophenyl)pentyl-N-methyl-piperidinium iodide;
N(3-oxo-5-p-bromophenyl)pentyl-N-methyl-piperidinium iodide;
N(3-oxo-5-o-bromophenyl)pentyl-N-methyl-piperidinium iodide;

N(3-oxo-5-p-chlorophenyl)pentyl-N-methyl-
  piperidinium iodide;
N(3-oxo-5-p-methylphenyl)pentyl-N-methyl-
  piperidinium iodide;
N(3-oxo-5-[3,4-dimethyl]phenyl)pentyl-N-methyl-
  piperidinium iodide;
N(3-oxo-5-p-ethylphenyl)pentyl-N-methylpiperidinium
  iodide;
N(3-oxo-5-[3,4-diethyl]phenyl)pentyl-N-methyl-
  piperidinium iodide;
N(3-oxo-5-p-butylphenyl)pentyl-N-methylpiperidinium
  iodide;
N(3-oxo-5-p-hexylphenyl)pentyl-N-methylpiperidinium
  iodide;
N(3-oxo-5-p-ethoxyphenyl)pentyl-N-methyl-
  piperidinium iodide;
N(3-oxo-5-[3,4-diethoxy]phenyl)pentyl-N-methyl
  piperidinium iodide, and others.

All these, and other appropriately substituted benzaldehydes are commercially available, for example, from Aldrich, Fisher, American-Biosynthetics, Biochemical Laboratories, Chemservice, Research Organic/Inorganic Chemicals and others.

PREPARATION 8

A. Preparation of
2,2-Dimethyl-5-(1,5-Dioxo-2-Aminoformyl-7-p-Methoxyphenyl)Heptyl-1,3-Benzoxathiole(IXX)

($R_1$ and $R_2$ are $CH_3$ and Y is 4—$OCH_3$)

This Preparation illustrates the process of making of starting material for compounds wherein X is $CH_2$—$CH_2$.

A solution of 5.16 g of 5-formamidoacetyl-2,2-dimethyl-1,3-benzoxathiole (IX) in 20 ml of dimethyl-formamide was stirred for 4 hours with 10 g of N(3-oxo-5-p-methoxyphenyl)-pentyl N-methylpiperidinium iodide and 6 g potassium carbonate. The reaction mixture was then quenched with water and dilute HCl and extracted twice with ethyl acetate. The extracts were combined, washed with brine, dried over $MgSO_4$ and evaporated to yield an oil which was chromatographed through silica gel eluting with ethyl acetate-hexane (2:1). Evaporation of the appropriate fractions yielded 2.3 g of 2,2-dimethyl-5-(1,5-dioxo-2-aminoformyl-7-p-methoxyphenyl)-heptyl-1,3-benzoxathiole (IXX) as a yellow oil.

| n.m.r. | 1.90 ppm (6 H; 2 × $CH_3$ |
| --- | --- |
|  | 1.5–2.9 (8H; 4 × $CH_2$ multiplets) |
|  | 3.80 (3H; $OCH_3$) |
|  | 5.60 (1H; CH—CH) |
|  | 6.80–8.25 (7H; Ar—H) |
|  | 7.88 (1H; CHO) |
| mass spec. | 440 ($m^+$—H |

B. Preparation of
2,2-Dimethyl-5-(1,5-Dioxo-2-Aminoformyl-7-Substituted Phenyl)Heptyl-1,3-Benzoxathioles (IXX)

To prepare other 2,2-dimethyl-5-(1,5-dioxo-2-aminoformyl-7-substituted phenyl)heptyl-1,3-benzoxathioles, N(3-oxo-5-p-methoxyphenyl)pentyl N-methylpiperidinium iodide is substituted with otherwise N(3-oxo-5-substituted phenyl)pentyl N-methylpiperidinium iodides prepared in Preparation 7.D.

Thus, when substituting into the Procedure 8.A. hereinabove for N(3-oxo-5-p-methoxyphenyl)pentyl-N-methylpiperidinium iodide one of the following compounds (Preparation 7.D.):
N(3-oxo-5-phenyl)pentyl-N-methylpiperidinium iodide;
N(3-oxo-5-p-fluorophenyl)pentyl-N-methyl-
  piperidinium iodide;
N(3-oxo-5-o-fluorophenyl)pentyl-N-methyl-
  piperidinium iodide;
N(3-oxo-5-p-bromophenyl)pentyl-N-methyl-
  piperidinium iodide;
N(3-oxo-5-o-bromophenyl)pentyl-N-methyl-
  piperidinium iodide;
N(3-oxo-5-p-chlorophenyl)pentyl-N-methyl-
  piperidinium iodide;
N(3-oxo-5-p-methylphenyl)pentyl-N-methyl-
  piperidinium iodide;
N(3-oxo-5-[3,4-dimethyl]phenyl)pentyl-N-methyl-
  piperidinium iodide;
N(3-oxo-5-p-ethylphenyl)pentyl-N-methylpiperidinium
  iodide;
N(3-oxo-5-[3,4-diethyl]phenyl)pentyl-N-methyl-
  piperidinium iodide;
N(3-oxo-5-p-butylphenyl)pentyl-N-methylpiperidinium
  iodide;
N(3-oxo-5-p-hexylphenyl)pentyl-N-methylpiperidinium
  iodide;
N(3-oxo-5-p-ethoxyphenyl)pentyl-N-methyl-
  piperidinium iodide;
N(3-oxo-5-[3,4-diethoxy]phenyl)pentyl-N-methyl-
  piperidinium iodide;
N(3-oxo-5-[3,4-methylenedioxy]phenyl)pentyl-N-methylpiperidinium iodide, or others;
one obtains, respectively:
2,2-dimethyl-5-(1,5-dioxo-2-aminoformyl-7-phenyl)-
  heptyl-1,3-benzoxathiole;
2,2-dimethyl-5-[1,5-dioxo-2-aminoformyl-7-(p-fluorophenyl)]heptyl-1,3-benzoxathiole;
2,2-dimethyl-5-[1,5-dioxo-2-aminoformyl-7-(o-fluorophenyl)]heptyl-1,3-benzoxathiole;
2,2-dimethyl-5-[1,5-dioxo-2-aminoformyl-7-(p-bromophenyl)]heptyl-1,3-benzoxathiole;
2,2-dimethyl-5-[1,5-dioxo-2-aminoformyl-7-(o-bromophenyl)]heptyl-1,3-benzoxathiole;
2,2-dimethyl-5-[1,5-dioxo-2-aminoformyl-7-(p-chlorophenyl)]heptyl-1,3-benzoxathiole;
2,2-dimethyl-5-[1,5-dioxo-2-aminoformyl-7-(p-methylphenyl)]heptyl-1,3-benzoxathiole;
2,2-dimethyl-5-[1,5-dioxo-2-aminoformyl-7-(3,4-dimethylphenyl)]heptyl-1,3-benzoxathiole;
2,2-dimethyl-5-[1,5-dioxo-2-aminoformyl-7-(p-ethylphenyl)]heptyl-1,3-benzoxathiole;
2,2-dimethyl-5-[1,5-dioxo-2-aminoformyl-7-(3,4-dimethylphenyl)]heptyl-1,3-benzoxathiole;
2,2-dimethyl-5-[1,5-dioxo-2-aminoformyl-7-(p-butylphenyl)]heptyl-1,3-benzoxathiole;
2,2-dimethyl-5-[1,5-dioxo-2-aminoformyl-7-(p-hexylphenyl)]heptyl-1,3-benzoxathiole;
2,2-dimethyl-5-[1,5-dioxo-2-aminoformyl-7-(p-ethoxyphenyl)]heptyl-1,3-benzoxathiole;
2,2-dimethyl-5-[1,5-dioxo-2-aminoformyl-7-(3,4-diethoxyphenyl)]heptyl-1,3-benzoxathiole;
2,2-dimethyl-5-[1,5-dioxo-2-aminoformyl-7-(3,4-methylenedioxyphenyl)]heptyl-1,3-benzoxathiole.

C. Preparation of
2,2-Disubstituted-5-(1,5-Dioxo-2-Aminoformyl-7-Substituted Phenyl)-Heptyl-1,3-Benzoxathioles To prepare other 2,2-disubstituted-5-(1,5-dioxo-2-aminoformyl-7-substituted phenyl)heptyl-1,3-benzoxathiole, the same procedure as described in Part B of this preparation is used, substituting 5-formamidoacetyl-2,2-dimethyl-1,3-benzoxathiole with compounds prepared in Preparation 6.B; and N(3-oxo-5-p-methoxyphenyl)-pentyl-N-methylpiperidinium iodide with other N(3-oxo-5-substituted)pentyl-N-methylpiperidinium iodides, prepared in Preparation 7.D.

When substituting in the procedure of Preparation 8.B. 5-formamido-2,2-dimethyl-1,3-benzoxathiole with 5-formamido-2,2-diethyl-1,3-benzoxathiole one obtains, respectively:

2,2-diethyl-5-(1,5-dioxo-2-aminoformyl-7-phenyl)heptyl-1,3-benzoxathiole;
2,2-diethyl-5-[1,5-dioxo-2-aminoformyl-7-(p-fluorophenyl)]heptyl-1,3-benzoxathiole;
2,2-diethyl-5-[1,5-dioxo-2-aminoformyl-7-(o-fluorophenyl)]heptyl-1,3-benzoxathiole;
2,2-diethyl-5-[1,5-dioxo-2-aminoformyl-7-(p-bromophenyl)]heptyl-1,3-benzoxathiole;
2,2-diethyl-5-[1,5-dioxo-2-aminoformyl-7-(o-bromophenyl)]heptyl-1,3-benzoxathiole;
2,2-diethyl-5-[1,5-dioxo-2-aminoformyl-7-(p-chlorophenyl)]heptyl-1,3-benzoxathiole;
2,2-diethyl-5-[1,5-dioxo-2-aminoformyl-7-(p-methylphenyl)]heptyl-1,3-benzoxathiole;
2,2-diethyl-5-[1,5-dioxo-2-aminoformyl-7-(3,4-dimethylphenyl)]heptyl-1,3-benzoxathiole;
2,2-diethyl-5-[1,5-dioxo-2-aminoformyl-7-(p-ethylphenyl)]heptyl-1,3-benzoxathiole;
2,2-diethyl-5-[1,5-dioxo-2-aminoformyl-7-(3,4-dimethylphenyl)]heptyl-1,3-benzoxathiole;
2,2-diethyl-5-[1,5-dioxo-2-aminoformyl-7-(p-butylphenyl)]heptyl-1,3-benzoxathiole;
2,2-diethyl-5-[1,5-dioxo-2-aminoformyl-7-(p-hexylphenyl)]heptyl-1,3-benzoxathiole;
2,2-diethyl-5-[1,5-dioxo-2-aminoformyl-7-(p-ethoxyphenyl)]heptyl-1,3-benzoxathiole;
2,2-diethyl-5-[1,5-dioxo-2-aminoformyl-7-(3,4-diethoxyphenyl)]heptyl-1,3-benzoxathiole;
2,2-diethyl-5-[1,5-dioxo-2-aminoformyl-7-(3,4-methylenedioxyphenyl)]heptyl-1,3-benzoxathiole.

When substituting in the procedure of Preparation 8.B. 5-formamido-2,2-dimethyl-1,3-benzoxathiole with 5-formamido-2,2-di-n-propyl-1,3-benzoxathiole; one obtains, respectively:

2,2-di-n-propyl-5-(1,5-dioxo-2-aminoformyl-7-phenyl)-heptyl-1,3-benzoxathiole;
2,2-di-n-propyl-5-[1,5-dioxo-2-aminoformyl-7-(p-fluorophenyl)]heptyl-1,3-benzoxathiole;
2,2-di-n-propyl-5-[1,5-dioxo-2-aminoformyl-7-(o-fluorophenyl)]heptyl-1,3-benzoxathiole;
2,2-di-n-propyl-5-[1,5-dioxo-2-aminoformyl-7-(p-bromophenyl)]heptyl-1,3-benzoxathiole;
2,2-di-n-propyl-5-[1,5-dioxo-2-aminoformyl-7-(o-bromophenyl)]heptyl-1,3-benzoxathiole;
2,2-di-n-propyl-5-[1,5-dioxo-2-aminoformyl-7-(p-chlorophenyl)]heptyl-1,3-benzoxathiole;
2,2-di-n-propyl-5-[1,5-dioxo-2-aminoformyl-7-(p-methylphenyl)]heptyl-1,3-benzoxathiole;
2,2-di-n-propyl-5-[1,5-dioxo-2-aminoformyl-7-(3,4-dimethylphenyl)]heptyl-1,3-benzoxathiole;
2,2-di-n-propyl-5-[1,5-dioxo-2-aminoformyl-7-(p-ethylphenyl)]heptyl-1,3-benzoxathiole;
2,2-di-n-propyl-5-[1,5-dioxo-2-aminoformyl-7-(3,4-dimethylphenyl)]heptyl-1,3-benzoxathiole;
2,2-di-n-propyl-5-[1,5-dioxo-2-aminoformyl-7-(p-butylphenyl)]heptyl-1,3-benzoxathiole;
2,2-di-n-propyl-5-[1,5-dioxo-2-aminoformyl-7-(p-hexylphenyl)]heptyl-1,3-benzoxathiole;
2,2-di-n-propyl-5-[1,5-dioxo-2-aminoformyl-7-(p-ethoxyphenyl)]heptyl-1,3-benzoxathiole;
2,2-di-n-propyl-5-[1,5-dioxo-2-aminoformyl-7-(3,4-diethoxyphenyl)]heptyl-1,3-benzoxathiole; and
2,2-di-n-propyl-5-[1,5-dioxo-2-aminoformyl-7-(3,4-methylenedioxyphenyl)]heptyl-1,3-benzoxathiole.

When substituting in the procedure of Preparation 8.B. 5-formamido-2,2-dimethyl-1,3-benzoxathiole with 5-formamido-2,2-di-n-butyl-1,3-benzoxathiole; one obtains, respectively:

2,2-di-n-butyl-5-(1,5-dioxo-2-aminoformyl-7-phenyl)-heptyl-1,3-benzoxathiole;
2,2-di-n-butyl-5-[1,5-dioxo-2-aminoformyl-7-(p-fluorophenyl)]heptyl-1,3-benzoxathiole;
2,2-di-n-butyl-5-[1,5-dioxo-2-aminoformyl-7-(o-fluorophenyl)]heptyl-1,3-benzoxathiole;
2,2-di-n-butyl-5-[1,5-dioxo-2-aminoformyl-7-(p-bromophenyl)]heptyl-1,3-benzoxathiole;
2,2-di-n-butyl-5-[1,5-dioxo-2-aminoformyl-7-(o-bromophenyl)]heptyl-1,3-benzoxathiole;
2,2-di-n-butyl-5-[1,5-dioxo-2-aminoformyl-7-(p-chlorophenyl)]heptyl-1,3-benzoxathiole;
2,2-di-n-butyl-5-[1,5-dioxo-2-aminoformyl-7-(p-methylphenyl)]heptyl-1,3-benzoxathiole;
2,2-di-n-butyl-5-[1,5-dioxo-2-aminoformyl-7-(3,4-dimethylphenyl)]heptyl-1,3-benzoxathiole;
2,2-di-n-butyl-5-[1,5-dioxo-2-aminoformyl-7-(p-ethylphenyl)]heptyl-1,3-benzoxathiole;
2,2-di-n-butyl-5-[1,5-dioxo-2-aminoformyl-7-(3,4-dimethylphenyl)]heptyl-1,3-benzoxathiole;
2,2-di-n-butyl-5-[1,5-dioxo-2-aminoformyl-7-(p-butylphenyl)]heptyl-1,3-benzoxathiole;
2,2-di-n-butyl-5-[1,5-dioxo-2-aminoformyl-7-(p-hexylphenyl)]heptyl-1,3-benzoxathiole;
2,2-di-n-butyl-5-[1,5-dioxo-2-aminoformyl-7-(p-ethoxyphenyl)]heptyl-1,3-benzoxathiole;
2,2-di-n-butyl-5-[1,5-dioxo-2-aminoformyl-7-(3,4-diethoxyphenyl)]heptyl-1,3-benzoxathiole; and
2,2-di-n-butyl-5-[1,5-dioxo-2-aminoformyl-7-(3,4-methylenedioxyphenyl)]heptyl-1,3-benzoxathiole.

D. Compounds named above are the exemplary compounds only, illustrating the procedure of preparations of compounds with various $R_1$, $R_2$ and Y substituents. Other compounds, wherein $R_1$ substituent is —H, other lower alkyl or cycloalkyl than those illustrated above, or those wherein $R_2$ substituent is —H, other lower alkyl or cycloalkyl than those illustrated above, and wherein $R_1$ and $R_2$ are not equivalent each may be in cis- or trans- position, may be prepared by following the procedure of Preparation 8.A. and B.

Similarly, compounds substituted on Y with substituents other than those illustrated above such as lower alkyls, or —$OR_3$, where $R_3$ is H or lower alkyl, may be prepared by the following procedure of Sections A. and B. of this preparation. Also, Y substituents can be in the ortho, meta or para position and when a is 2, they may differ or both may be the same.

PREPARATION 9

A. Preparation of 2,2-Dimethyl-5-(1,5-Dioxo-2-Aminoformyl-7-Phenyl)-Hept-6-enyl-1,3-Benzoxathiole (IXX)

(X is CH=CH and Y is Hydrogen)

This preparation illustrates the process of making starting material for compounds wherein X is CH=CH.

A mixture of 4.0 g 5-formamidoacetyl-2,2-dimethyl-1,3-benzoxathiole (IX) 9.6 g N-oxo-5-phenylpent-4-ene-1-yl-N-methylpiperidinium iodine, and 4.4 g potassium carbonate was stirred in 20 ml of dimethylformamide. After 6 hours the mixture was mixed with Celite, water and ethyl acetate. The mixture was filtered and the organic layer separated, dried and evaporated. The residue was chromatographed on silica gel eluting with ethyl acetate-hexane (1:1) to yield 3.5 g of 2,2-dimethyl-5-(1,5-dioxo-2-aminoformyl-7-phenyl)hept-6-enyl-1,3-benzoxathiole (IXX) as a yellow oil.

B. Preparation of Other 2,2-Disubstituted-5-(1,5-Dioxo-2-Aminoformyl-7-Phenyl)Hept-6-enyl-1,3-Benzoathioles Similarly following the Preparation 10.A., but substituting 5-formamidoacetyl-2,2-dimethyl- 1,3-benzoxathiole (IX) with compounds obtained in sections B. and C. of Preparation 8, the other alkenyl benzoxathiole compounds may be prepared.

PREPARATION 10

A. Preparation of 2,2-Dimethyl-5-(1,5-Dioxo-2-Aminoformyl-(7-Phenyl)-Hept-6-ynyl-1,3-Benzoxathiole(IXX)

(X is C≡C and Y is 4—OCH$_3$)

Similarly, substituting N(3-oxo-5-p-methoxyphenyl)-pentyl-N-methylpiperidinium iodide in the procedure of Preparation 8.A for N(3-oxo-5-p-methoxyphenyl)pent-4-ynyl-N-methylpiperidinium iodide, the title compound 2,2-dimethyl-5-(1,5-dioxo-2-aminoformyl-7-phenyl)hept-6-ynyl-1,3-benzoxathiole may be prepared.

B. Preparation of Other 2,2-Disubstituted 5-(1,5-Dioxo-2-Aminoformyl-7-Substituted Phenyl)Hept-6-ynyl-1,3-Benzoxathiole The other benzoxathiole compounds may be prepared similarly to the Preparations 8.A., 8.B., and 8.C.

PREPARATION 11

A. Preparation of 2,2-Spirocyclopentane-5-Carboxy-1,3-Benzoxathiole (IV)(R$_1$ and R$_2$ is (CH$_2$)$_4$)

16 g of 3-mercapto-4-hydroxybenzoic acid obtained by a procedure of Preparation 2 was dissolved in a mixture of 300 ml of toluene and 50 ml of cyclopentanone. 50 ml of boron trifluoride etherate was added and the mixture was stirred at room temperature for 4 hours. Ice (50 g) was added and the mixture stirred for a further 1 hour. The organic layer was separated, washed with brine, dried with magnesium sulfate and evaporated to leave a solid residue. The residue was recrystallized from aqueous methanol to yield 15 g of 2,2-spirocyclopentane-5-carboxy-1,3-benzoxathiole, m.p. 180°–183° C.

B. Preparation of 2,2-Spirocycloalkane-5-Carboxy-1,3-Benzoxathioles

Similarly to the Preparation 12.A.,
2,2-spirocyclobutane-5-carboxy-1,3-benzoxathiole;
2,2-spirocyclohexane-5-carboxy-1,3-benzoxathiole; and
2,2-spirocycloheptane-5-carboxy-1,3-benzoxathiole
are prepared by following the procedure of Preparation 11.A. but substituting cyclopentanone with cyclobutanone, cyclohexanone or cycloheptanone.

PREPARATION 12

A. Preparation of 2,2-Spirocyclopentane-5-Chloroacetyl-1,3-Benzoxathiole (VII) (R$_1$ and R$_2$ are (CH$_2$)$_4$)

A mixture consisting of 10 g of 2,2-spirocyclopentane-5-chloroacetyl-1,3-benzoxathiole, (Preparation 11), 10 g of oxalyl chloride and 20 ml of ether was boiled gently for 2 hours. The solution was cooled and evaporated and the residue was added to an ether solution of diazomethane prepared from 25 g of N-nitroso-N-methyl urea. After stirring for 18 hours at room temperature the solution was acidified with methanolic hydrogen chloride and then evaporated to leave a solid residue which was recrystallized from ether/hexane to yield 6 g of 2,2-spirocyclopentane-5-chloroacetyl-1,3-benzoxathiole, m.p. 120°–121° C.

B. Preparation of 2,2-Spirocycloalkane-5-Carboxy-1,3-Benzoxathioles

Similarly to the Preparation 12.A.,
2,2-spirocyclobutane-5-chloroacetyl-1,3-benzoxathiole;
2,2-spirocyclohexane-5-chloroacetyl-1,3-benzoxathiole; and
2,2-spirocycloheptane-5-chloroacetyl-1,3-benzoxathiole
are prepared by following the procedure of Preparation 12.A. but substituting the starting compound of this preparation with compounds prepared by Preparation 11.B.

PREPARATION 13

A. Preparation of 2,2-Spirocyclopentane-5-Azidoacetyl-1,3-Benzoxathiole (VIII)(R$_1$ and R$_2$ are (CH$_2$)$_4$)

A solution of 20 g of 2,2-spirocyclopentane-5-chloroacetyl-1,3-benzoxathiole in acetonitrile (100 ml) was stirred for two days with 7 g of finely powdered sodium azide. The reaction mixture was filtered, evaporated and the residue recrystallized from methanol to yield 12 g of 2,2-spirocyclopentane-5-azidoacetyl-1,3-benzoxathiole, m.p. 86°–87° C.

B. Preparation of 2,2-Spirocycloalkane-5-Azidoacetyl-1,3-Benzoxathioles

Similarly to the Preparation 13.A.,
2,2-spirocyclobutane-5-azidoacetyl-1,3-benzoxathiole;
2,2-spirocyclohexane-5-azidoacetyl-1,3-benzoxathiole; and
2,2-spirocycloheptane-5-azidoacetyl-1,3-benzoxathiole
are prepared by following the procedure of Preparation 13.A. but substituting the starting compound of this preparation with compounds prepared in Preparation 12.B.

PREPARATION 14

A. Preparation of 2,2-Spirocyclopentane-5-Formamido-Acetyl-1,3-Benzoxathiole (IX)

(R$_1$ and R$_2$ are (CH$_2$)$_4$ and Y is Hydrogen)

10 g of 2,2-spirocyclopentane-5-azidoacetyl-1,3-benzoxathiole was added portionwise to a cooled solution of 20 g stannous chloride and 7 g sodium formate in 16 ml of acetic-formic anhydride and 9 ml of formic acid. After 24 hours at room temperature the mixture was quenched with ice and dilute hydrochloric acid and extracted with ethyl acetate. The mixture was dried over MgSO$_4$, evaporated, and the residue purified by chromatography through a column of silica gel eluting with ethyl acetate-hexane (1:1) to yield 6 g of 2,2-spirocyclopentane-5-formamidoacetyl-1,3-benzoxathiole, m.p. 143°–145° C.

B. Preparation of 2,2-Spirocycloalkane-5-Formamido-Acetyl-1,3-Benzoxathioles Similarly to the Preparation 14.A.,
2,2-spirocyclobutane-5-formamidoacetyl-1,3-benzoxathiole;
2,2-spirocyclohexane-5-formamidoacetyl-1,3-benzoxathiole; and
2,2-spirocycloheptane-5-formamidoacetyl-1,3-benzoxathiole
are prepared by following the procedure of Preparation 14.A. but substituting the starting compound of this preparation with compounds prepared in Preparation 13.B.

PREPARATION 15

A. Preparation of 2,2-Spirocyclopentane-5-(1,5-Dioxo-2-Aminoformyl-7-p-Methoxyphenyl)Heptane-1,3-Benzoxathiole (IXX)

(R$_1$ and R$_2$ are (CH$_2$)$_4$; X is (CH$_2$) Y is 4—OCH$_3$)

A solution of 5.16 of 2,2-spirocyclopentane-5-formamidoacetyl-1,3-benzoxathiole in dimethylformamide (20 ml) was stirred for 4 hours with N(3-oxo-5-p-methoxyphenyl)pentyl-N-methylpiperidinium iodide (10 g) and potassium carbonate (6 g). The reaction mixture was quenched with water and dilute hydrochloric acid and extracted twice with ethyl acetate. The extracts were combined, washed with brine, dried with MgSO$_4$ and evaporated to yield an oil which was chromatographed through silica gel eluting with ethyl acetate-hexane (2:1). Evaporation of the appropriate fractions yielded 2.3 g of 2,2-spirocyclopentane-5-(1,5-dioxo-2-aminoformyl-7-p-methoxyphenyl)heptane-1,3-benzoxathiole as an oil.

B. Preparation of 2,2-Spirocycloalkane-5-(1,5-Dioxo-2-Aminoformyl-7-p-Methoxyphenyl)Heptane-1,3-Benzoxathioles (IXX)

Similarly to the Preparation 15.A.,
2,2-spirocyclobutane-5-(1,5-dioxo-2-aminoformyl-7-(p-methoxyphenyl))heptane-1,3-benzoxathiole;
2,2-spirocyclohexane-5-(1,5-dioxo-2-aminoformyl-7-(p-methoxyphenyl))heptane-1,3-benzoxathiole; and
2,2-spirocycloheptane-5-(1,5-dioxo-2-aminoformyl-7-(p-methoxyphenyl))heptane-1,3-benzoxathiole
are prepared by following the procedure of Preparation 15.A. but substituting the starting compound of this preparation with compounds prepared in Preparation 14.B.

C. Preparation of 2,2-Spirocycloalkane-5-(1,5-Dioxo-2-Aminoformyl-7-Substituted Phenyl)Heptane-1,3-Benzoxathioles Similarly, to the procedure of Preparation 8.B. and 8.C., one can substitute into the procedure of Preparations 14.A. and 14.B. various N(3-oxo-(Y)$_a$-substituted phenyl)-N-methylpiperidinium iodides to obtain various spirocycloalkane compounds of various carbon chain length and phenyl substitution.

PREPARATION 16

A. Preparation of 2,2-Spirocyclopentane-5-(1,5-Dioxo-2-Aminoformyl-7-phenyl)Hept-6-ene-1,3-Benzoxathiole (IXX)

(R$_1$ and R$_2$ are (CH$_2$)$_4$; X is CH=CH; Y is —H—)

A mixture of 4.0 g 2,2-spirocyclopentane-5-formamidoacetyl-1,3-benzoxathiole, 9.6 g N-oxo-5-phenylpent-4-en-1-yl-N-methylpiperidinium iodide, and 4.4 g potassium carbonate was stirred in 20 ml of dimethylformamide. After 6 hours the mixture was mixed with Celite, water and ethyl acetate. The mixture was filtered and the organic layer separated, dried and evaporated. The residue was chromatographed on silica gel eluting with ethyl acetate-hexane (1:1) to yield 2,2-spirocyclopentane-5-[1,5-dioxo-2-aminoformyl-7-phenyl]hept-6-enyl-1,3-benzoxathiole.

B. Preparation of 2,2-Spirocycloalkane-5-(1,5-Dioxo-2-Aminoformyl-7-p-Methoxyphenyl)-Hept-6-ene-1,3-Benzoxathioles Similarly to the Preparation 16.A.,
2,2-spirocyclobutane-5-(1,5-dioxo-2-aminoformyl-7-(p-methoxyphenyl))-hept-6-enyl-1,3-benzoxathiole;
2,2-spirocyclohexane-5-(1,5-dioxo-2-aminoformyl-7-(p-methoxyphenyl))-hept-6-enyl-1,3-benzoxathiole; and
2,2-spirocycloheptane-5-(1,5-dioxo-2-aminoformyl-7-(p-methoxyphenyl))-hept-6-enyl-1,3-benzoxathiole
are prepared, by following the procedure of Preparation 16.A. but substituting the starting compound of this preparation, i.e., 2,2-spirocyclopentane-5-formamidoacetyl-1,3-benzoxathiole with compounds prepared in Preparation 14.B. or 14.C.

PREPARATION 17

A. Preparation of 2,2-Spirocyclopentane-5-(1,5-Dioxo-2-Aminoformyl-7-Phenyl)-Hept-6-yne-1,3-Benzoxathiole (IXX)

(R$_1$ and R$_2$ are (CH$_2$)$_4$; X is C≡C; Y is Hydrogen)

A mixture of 4.0 g 2,2-spirocyclopentane-5-formamido-1,3-benzoxathiole, 9.6 g of N-oxo-5-phenylpent-4-yn-1-yl-N-methylpiperidinium iodine, and 4.4 g potassium carbonate was stirred in 20 ml of dimethylformamide. After 6 hours the mixture was mixed with Celite, water and ethyl acetate. The mixture was filtered and the organic layer separated, dried and evaporated. The residue was chromatographed on silica gel eluting with ethyl acetate-hexane (1:1) to yield 2,2-spirocyclopentane-5-(1,5-dioxo-2-aminoformyl-7-phenyl)-hept-6-yne-1,3-benzoxathiole.

B. Preparation of 2,2-Spirocycloalkane-5-(1,5-Dioxo-2-Aminoformyl-7-p-Methoxyphenyl)Hept-6-yne-1,3-Benzoxathioles Similarly to the Preparation 17.A.,
2,2-spirocyclobutane-5-(1,5-dioxo-2-aminoformyl-7-(p-methoxyphenyl))hept-6-yne-1,3-benzoxathiole;
2,2-spirocyclohexane-5-(1,5-dioxo-2-aminoformyl-7-(p-methoxyphenyl))hept-6-yne-1,3-benzoxathiole; and
2,2-spirocycloheptane-5-(1,5-dioxo-2-aminoformyl-7-(p-methoxyphenyl))hept-6-yne-1,3-benzoxathiole
are prepared by following the procedure of Preparation 17.A. but substituting the starting compound of this preparation with compounds prepared in Preparation 14.B.

EXAMPLE 1

A. Preparation of 2-(p-Methoxyphenethyl)-5-(2,2-Dimethyl-1,3-Benzoxathiole-5-yl Hydroxymethyl) Pyrrolidine Hydrochloride (XXI)

($R_1$ and $R_2$ are $CH_3$; X is $(CH_2)_2$; Y is 4—$OCH_3$)

3 g of 2,2-dimethyl-5-(1,5-dioxo-2-aminoformyl-7-p-methoxyphenyl)heptyl-1,3-benzoxathiole obtained by Preparation 7.A. was dissolved in 10 ml of methanol, and 10 ml of concentrated hydrochloric acid was added. The solution was stirred for 24 hours at room temperature, then evaporated to yield an oily residue which was dissolved in methanol (50 ml). The solution was cooled to about −40° C. with a dry ice acetone bath and then treated with 300 mg of sodium borohydride. The solution was allowed to warm to room temperature and then evaporated. The residue was treated with ammonium chloride solution and ethyl acetate. The organic layer was separated, dried over potassium carbonate and evaporated to leave a residue which was dissolved in methanol. The solution was acidified by cautious addition of a solution of hydrogen chloride in methanol. Evaporation of the solvent yielded an oil which was crystallized from acetonitrile-ethyl acetate. Yield was 2 g of 2-(p-methoxyphenethyl)-5-(2,2-dimethyl-1,3-benzoxathiole-5-yl-hydroxymethyl)pyrrolidine hydrochloride (XXI), m.p. 210°–211° C.

B. Preparation of Other 2-Substituted-5-(2,2-Disubstituted-1,3-Benzoxathiole-5-yl-Hydroxymethyl)Pyrrolidines Similarly, following the procedure of Example 1.A. but substituting 2,2-dimethyl-5-(1,5-dioxo-2-aminoformyl-7-p-methoxyphenyl)heptyl-1,3-benzoxathiole with one of the following compounds (Preparation 8.B.):
2,2-dimethyl-5(1,5-dioxo-2-aminoformyl-7-(phenyl)-)heptyl-1,3-benzoxathiole;
2,2-dimethyl-5(1,5-dioxo-2-aminoformyl-7-(p-fluorophenyl))heptyl-1,3-benzoxathiole;
2,2-dimethyl-5(1,5-dioxo-2-aminoformyl-7-(o-fluorophenyl))heptyl-1,3-benzoxathiole;
2,2-dimethyl-5(1,5-dioxo-2-aminoformyl-7-(p-bromophenyl))heptyl-1,3-benzoxathiole;
2,2-dimethyl-5(1,5-dioxo-2-aminoformyl-7-(o-bromophenyl))heptyl-1,3-benzoxathiole;
2,2-dimethyl-5(1,5-dioxo-2-aminoformyl-7-(p-chlorophenyl))heptyl-1,3-benzoxathiole;
2,2-dimethyl-5(1,5-dioxo-2-aminoformyl-7-(p-methylphenyl))heptyl-1,3-benzoxathiole;
2,2-dimethyl-5(1,5-dioxo-2-aminoformyl-7-(3,4-dimethylphenyl))heptyl-1,3-benzoxathiole;
2,2-dimethyl-5(1,5-dioxo-2-aminoformyl-7-(p-ethylphenyl))heptyl-1,3-benzoxathiole;
2,2-dimethyl-5(1,5-dioxo-2-aminoformyl-7-(3,4-dimethylphenyl))heptyl-1,3-benzoxathiole;
2,2-dimethyl-5(1,5-dioxo-2-aminoformyl-7-(p-butylphenyl))heptyl-1,3-benzoxathiole;
2,2-dimethyl-5(1,5-dioxo-2-aminoformyl-7-(p-hexylphenyl))heptyl-1,3-benzoxathiole;
2,2-dimethyl-5(1,5-dioxo-2-aminoformyl-7-(p-ethoxyphenyl))heptyl-1,3-benzoxathiole;
2,2-dimethyl-5(1,5-dioxo-2-aminoformyl-7-(3,4-diethoxyphenyl))heptyl-1,3-benzoxathiole;
2,2-dimethyl-5(1,5-dioxo-2-aminoformyl-7-(3,4-methylenedioxyphenyl))heptyl-1,3-benzoxathiole, or others;

one obtains, respectively:
2-(phenethyl)-5(2,2-dimethyl-1,3-benzoxathiol-5-yl)hydroxymethylpyrrolidine hydrochloride;
2-(p-fluorophenethyl)-5(2,2-dimethyl-1,3-benzoxathiol-5-yl)hydroxymethylpyrrolidine hydrochloride;
2-(o-fluorophenethyl)-5(2,2-dimethyl-1,3-benzoxathiol-5-yl)hydroxymethylpyrrolidine hydrochloride;
2-(p-bromophenethyl)-5(2,2-dimethyl-1,3-benzoxathiol-5-yl)hydroxymethylpyrrolidine hydrochloride;
2-(o-bromophenethyl)-5(2,2-dimethyl-1,3-benzoxathiol-5-yl)hydroxymethylpyrrolidine hydrochloride;
2-(p-chlorophenethyl)-5(2,2-dimethyl-1,3-benzoxathiol-5-yl)hydroxymethylpyrrolidine hydrochloride;
2-(p-methylphenethyl)-5(2,2-dimethyl-1,3-benzoxathiol-5-yl)hydroxymethylpyrrolidine hydrochloride;
2-(3,4-dimethylphenethyl)-5(2,2-dimethyl-1,3-benzoxathiol-5-yl)hydroxymethylpyrrolidine hydrochloride;
2-(p-ethylphenethyl)-5(2,2-dimethyl-1,3-benzoxathiol-5-yl)hydroxymethylpyrrolidine hydrochloride;
2-(3,4-diethylphenethyl)-5(2,2-dimethyl-1,3-benzoxathiol-5-yl)hydroxymethylpyrrolidine hydrochloride;
2-(p-butylphenethyl)-5(2,2-dimethyl-1,3-benzoxathiol-5-yl)hydroxymethylpyrrolidine hydrochloride;
2-(p-hexylphenethyl)-5(2,2-dimethyl-1,3-benzoxathiol-5-yl)hydroxymethyl pyrrolidine hydrochloride;
2-(p-ethoxyphenethyl)-5(2,2-dimethyl-1,3-benzoxathiol-5-ylhydroxymethyl)pyrrolidine hydrochloride;
2-(3,4-diethoxyphenethyl)-5(2,2-dimethyl-1,3-benzoxathiol-5-yl)hydroxymethylpyrrolidine hydrochloride;
2-(3,4-methylenedioxyphenethyl)-5-(2,2-dimethyl-1,3-benzoxathiole-5-yl)hydroxymethylpyrrolidine hydrochloride, or others.

Similarly, following the procedure of Example 1.A. but substituting 2,2-dimethyl-5-(1,5-dioxo-2-aminoformyl-7-p-methoxyphenyl)heptane-1,3-benzoxathiole with one of the following compounds (Preparation 8.C):
2,2-diethyl-5-(1,5-dioxo-2-aminoformyl-7-(phenyl))heptyl-1,3-benzoxathiole;
2,2-diethyl-5-(1,5-dioxo-2-aminoformyl-7-(p-fluorophenyl))heptyl-1,3-benzoxathiole;
2,2-diethyl-5-(1,5-dioxo-2-aminoformyl-7-(o-fluorophenyl))heptyl-1,3-benzoxathiole;
2,2-diethyl-5-(1,5-dioxo-2-aminoformyl-7-(p-bromophenyl))heptyl-1,3-benzoxathiole;
2,2-diethyl-5-(1,5-dioxo-2-aminoformyl-7-(o-bromophenyl))heptyl-1,3-benzoxathiole;
2,2-diethyl-5-(1,5-dioxo-2-aminoformyl-7-(p-chlorophenyl))heptyl-1,3-benzoxathiole;
2,2-diethyl-5-(1,5-dioxo-2-aminoformyl-7-(p-methylphenyl))heptyl-1,3-benzoxathiole;
2,2-diethyl-5-(1,5-dioxo-2-aminoformyl-7-(3,4-dimethylphenyl))heptyl-1,3-benzoxathiole;
2,2-diethyl-5-(1,5-dioxo-2-aminoformyl-7-(p-ethylphenyl))heptyl-1,3-benzoxathiole;
2,2-diethyl-5-(1,5-dioxo-2-aminoformyl-7-(3,4-diethylphenyl))heptyl-1,3-benzoxathiole;
2,2-diethyl-5-(1,5-dioxo-2-aminoformyl-7-(p-butylphenyl))heptyl-1,3-benzoxathiole;
2,2-diethyl-5-(1,5-dioxo-2-aminoformyl-7-(p-hexylphenyl))heptyl-1,3-benzoxathiole;
2,2-diethyl-5-(1,5-dioxo-2-aminoformyl-7-(p-ethoxyphenyl))heptyl-1,3-benzoxathiole;
2,2-diethyl-5-(1,5-dioxo-2-aminoformyl-7-(3,4-diethoxyphenyl))heptyl-1,3-benzoxathiole;
2,2-diethyl-5-(1,5-dioxo-2-aminoformyl-7-(3,4-methylenedioxyphenyl))heptyl-1,3-benzoxathiole, or others;

one obtains, respectively:

2-(phenethyl)-5(2,2-diethyl-1,3-benzoxathiol-5-yl)hydroxymethylpyrrolidine hydrochloride;

2-(p-fluorophenethyl)-5(2,2-diethyl-1,3-benzoxathiol-5-yl)hydroxymethylpyrrolidine hydrochloride;

2-(o-fluorophenethyl)-5(2,2-diethyl-1,3-benzoxathiol-5-yl)hydroxymethylpyrrolidine hydrochloride;

2-(p-bromophenethyl)-5(2,2-diethyl-1,3-benzoxathiol-5-yl)hydroxymethylpyrrolidine hydrochloride;

2-(o-bromophenethyl)-5(2,2-diethyl-1,3-benzoxathiol-5-yl)hydroxymethylpyrrolidine hydrochloride;

2-(p-chlorophenethyl)-5(2,2-diethyl-1,3-benzoxathiol-5-yl)hydroxymethylpyrrolidine hydrochloride;

2-(p-methylphenethyl)-5(2,2-diethyl-1,3-benzoxathiol-5-yl)hydroxymethylpyrrolidine hydrochloride;

2-(3,4-dimethylphenethyl)-5(2,2-diethyl-1,3-benzoxathiol-5-yl)hydroxymethylpyrrolidine hydrochloride;

2-(p-ethylphenethyl)-5(2,2-diethyl-1,3-benzoxathiol-5-yl)hydroxymethylpyrrolidine hydrochloride;

2-(3,4-diethylphenethyl)-5(2,2-diethyl-1,3-benzoxathiol-5-yl)hydroxymethylpyrrolidine hydrochloride;

2-(p-butylphenethyl)-5(2,2-diethyl-1,3-benzoxathiol-5-yl)hydroxymethylpyrrolidine hydrochloride;

2-(p-hexylphenethyl)-5(2,2-diethyl-1,3-benzoxathiol-5-yl)hydroxymethylpyrrolidine hydrochloride;

2-(p-ethoxyphenethyl)-5(2,2-diethyl-1,3-benzoxathiol-5-yl)hydroxymethylpyrrolidine hydrochloride;

2-(3,4-diethoxyphenethyl)-5(2,2-diethyl-1,3-benzoxathiol-5-yl)hydroxymethylpyrrolidine hydrochloride;

2-(3,4-methylenedioxyphenethyl)-5-(2,2-diethyl-1,3-benzoxathiol-5-yl)hydroxymethylpyrrolidine hydrochloride, or others.

Similarly, following the procedure of Example 1.A. but substituting 2,2-dimethyl-5-(1,5-dioxo-2-aminoformyl-7p-methoxyphenyl)heptyl-1,3-benzoxathiole with one of the following compounds (Preparation 8.C.:

2,2-di-n-propyl-5(1,5-dioxo-2-aminoformyl-7-(phenyl))heptyl-1,3-benzoxathiole;

2,2-di-n-propyl-5(1,5-dioxo-2-aminoformyl-7-(p-fluorophenyl))heptyl-1,3-benzoxathiole;

2,2-di-n-propyl-5(1,5-dioxo-2-aminoformyl-7-(o-fluorophenyl))heptyl-1,3-benzoxathiole;

2,2-di-n-propyl-5(1,5-dioxo-2-aminoformyl-7-(p-bromophenyl))heptyl-1,3-benzoxathiole;

2,2-di-n-propyl-5(1,5-dioxo-2-aminoformyl-7-(o-bromophenyl))heptyl-1,3-benzoxathiole;

2,2-di-n-propyl-5(1,5-dioxo-2-aminoformyl-7-(p-chlorophenyl))heptyl-1,3-benzoxathiole;

2,2-di-n-propyl-5(1,5-dioxo-2-aminoformyl-7-(p-methylphenyl))heptyl-1,3-benzoxathiole;

2,2-di-n-propyl-5[1,5-dioxo-2-aminoformyl-7-(3.4-dimethylphenyl)]heptyl-1,3-benzoxathiole, 2,2-di-n-propyl-5(1,5-dioxo-2-aminoformyl-7-(p-ethylphenyl))heptyl-1,3-benzoxathiole;

2,2-di-n-propyl-5(1,5-dioxo-2-aminoformyl-7-(3,4-diethylphenyl))heptyl-1,3-benzoxathiole;

2,2-di-n-propyl-5(1,5-dioxo-2-aminoformyl-7-(p-butylphenyl))heptyl-1,3-benzoxathiole;

2,2-di-n-propyl-5(1,5-dioxo-2-aminoformyl-7-(p-hexylphenyl))heptyl-1,3-benzoxathiole;

2,2-di-n-propyl-5(1,5-dioxo-2-aminoformyl-7-(p-ethoxyphenyl))heptyl-1,3-benzoxathiole;

2,2-di-n-propyl-5(1,5-dioxo-2-aminoformyl-7-(3,4-diethoxyphenyl))heptyl-1,3-benzoxathiole;

2,2-di-n-propyl-5(1,5-dioxo-2-aminoformyl-7-(3,4-methylenedioxy))heptyl-1,3-benzoxathiole, or others;

one obtains, respectively:

2-(phenethyl)-5(2,2-di-n-propyl-1,3-benzoxathiol-5-yl)hydroxymethylpyrrolidine hydrochloride;

2-(p-fluorophenethyl)-5(2,2-di-n-propyl-1,3-benzoxathiol-5-yl)hydroxymethylpyrrolidine hydrochloride;

2-(o-fluorophenethyl)-5(2,2-di-n-propyl-1,3-benzoxathiol-5-yl)hydroxymethylpyrrolidine hydrochloride;

2-(p-bromophenethyl)-5(2,2-di-n-propyl-1,3-benzoxathiol-5-yl)hydroxymethylpyrrolidine hydrochloride;

2-(o-bromophenethyl)-5(2,2-di-n-propyl-1,3-benzoxathiol-5-yl)hydroxymethylpyrrolidine hydrochloride;

2-(p-chlorophenethyl)-5(2,2-di-n-propyl-1,3-benzoxathiol-5-yl)hydroxymethylpyrrolidine hydrochloride;

2-(p-methylphenethyl)-5(2,2-di-n-propyl-1,3-benzoxathiol-5-yl)hydroxymethylpyrrolidine hydrochloride;

2-(3,4-dimethylphenethyl)-5(2,2-di-n-propyl-1,3-benzoxathiol-5-yl)hydroxymethylpyrrolidine hydrochloride;

2-(p-ethylphenethyl)-5(2,2-di-n-propyl-1,3-benzoxathiol-5-yl)hydroxymethylpyrrolidine hydrochloride;

2-(3,4-diethylphenethyl)-5(2,2-di-n-propyl-1,3-benzoxathiol-5-yl)hydroxymethylpyrrolidine hydrochloride;

2-(p-butylphenethyl)-5(2,2-di-n-propyl-1,3-benzoxathiol-5-yl)hydroxymethylpyrrolidine hydrochloride;

2-(p-hexylphenethyl)-5(2,2-di-n-propyl-1,3-benzoxathiol-5-yl)hydroxymethylpyrrolidine hydrochloride;

2-(p-ethoxyphenethyl)-5(2,2-di-n-propyl-1,3-benzoxathiol-5-yl)hydroxymethylpyrrolidine hydrochloride;

2-(3,4-diethoxyphenethyl)-5(2,2-di-n-propyl-1,3-benzoxathiol-5-yl)hydroxymethylpyrrolidine hydrochloride;

2-(3,4-methylenedioxyphenethyl)-5-(2,2-di-n-propyl-1,3-benzoxathiol-5-yl)hydroxymethylpyrrolidine hydrochloride, or others.

Similarly, following the procedure of Example 1.A. but substituting 2,2-dimethyl-5-(1,5-dioxo-2-aminoformyl7-p-methoxyphenyl)heptyl-1,3-benzoxathiole with one of the following compounds (Preparation 8.C.):

2,2-di-n-butyl-5(1,5-dioxo-2-aminoformyl-7-(phenyl))heptyl-1,3-benzoxathiole;

2,2-di-n-butyl-5(1,5-dioxo-2-aminoformyl-7-(p-fluorophenyl))heptyl-1,3-benzoxathiole;

2,2-di-n-butyl-5(1,5-dioxo-2-aminoformyl-7-(o-fluorophenyl))heptyl-1,3-benzoxathiole;

2,2-di-n-butyl-5(1,5-dioxo-2-aminoformyl-7-(p-bromophenyl))heptyl-1,3-benzoxathiole;

2,2-di-n-butyl-5(1,5-dioxo-2-aminoformyl-7-(o-bromophenyl))heptyl-1,3-benzoxathiole;

2,2-di-n-butyl-5(1,5-dioxo-2-aminoformyl-7-(p-chlorophenyl))heptyl-1,3-benzoxathiole;

2,2-di-n-butyl-5(1,5-dioxo-2-aminoformyl-7-(p-methylphenyl))heptyl-1,3-benzoxathiole;

2,2-di-n-butyl-5(1,5-dioxo-2-aminoformyl-7-(3,4-dimethylphenyl))heptyl-1,3-benzoxathiole;

2,2-di-n-butyl-5(1,5-dioxo-2-aminoformyl-7-(p-ethylphenyl))heptyl-1,3-benzoxathiole;

2,2-di-n-butyl-5(1,5-dioxo-2-aminoformyl-7-(3,4-diethylphenyl))heptyl-1,3-benzoxathiole;

2,2-di-n-butyl-5(1,5-dioxo-2-aminoformyl-7-(p-butylphenyl))heptyl-1,3-benzoxathiole;

2,2-di-n-butyl-5(1,5-dioxo-2-aminoformyl-7-(p-hexylphenyl))heptyl-1,3-benzoxathiole;

2,2-di-n-butyl-5(1,5-dioxo-2-aminoformyl-7-(p-ethoxyphenyl))heptyl-1,3-benzoxathiole;

2,2-di-n-butyl-5(1,5-dioxo-2-aminoformyl-7-(3,4-diethoxyphenyl))heptyl-1,3-benzoxathiole;

2,2-di-n-butyl-5[1,5-dioxo-2-aminoformyl-7-(3,4-methylenedioxyphenyl)]heptyl1,3-benzoxathiole, or others;

one obtains, respectively:

2-(phenethyl)-5(2,2-di-n-butyl-1,3-benzoxathiol-5-yl)hydroxymethylpyrrolidine hydrochloride;

2-(p-fluorophenethyl)-5(2,2-di-n-butyl-1,3-benzoxathiol-5-yl)hydroxymethylpyrrolidine hydrochloride;

2-(o-fluorophenethyl)-5(2,2-di-n-butyl-1,3-benzoxathiol-5-yl)hydroxymethylpyrrolidine hydrochloride;

2-(p-bromophenethyl)-5(2,2-di-n-butyl-1,3-benzoxathiol-5-yl)hydroxymethylpyrrolidine hydrochloride;

2-(o-bromophenethyl)-5(2,2-di-n-butyl-1,3-benzoxathiol-5-yl)hydroxymethylpyrrolidine hydrochloride;

2-(p-chlorophenethyl)-5(2,2-di-n-butyl-1,3-benzoxathiol-5-yl)hydroxymethylpyrrolidine hydrochloride;

2-(p-methylphenethyl)-5(2,2-di-n-butyl-1,3-benzoxathiol-5-yl)hydroxymethylpyrrolidine hydrochloride;

2-(3,4-dimethylphenethyl)-5(2,2-di-n-butyl-1,3-benzoxathiol-5-yl)hydroxymethylpyrrolidine hydrochloride;

2-(p-ethylphenethyl)-5(2,2-di-n-butyl-1,3-benzoxathiol-5-yl)hydroxymethylpyrrolidine hydrochloride;

2-(3,4-diethylphenethyl)-5(2,2-di-n-butyl-1,3-benzoxathiol-5-yl)hydroxymethylpyrrolidine hydrochloride;

2-(p-butylphenethyl)-5(2,2-di-n-butyl-1,3-benzoxathiol-5-yl)hydroxymethylpyrrolidine hydrochloride;

2-(p-hexylphenethyl)-5(2,2-di-n-butyl-1,3-benzoxathiol-5-yl)hydroxymethylpyrrolidine hydrochloride;

2-(p-ethoxyphenethyl)-5(2,2-di-n-butyl-1,3-benzoxathiol-5-yl)hydroxymethylpyrrolidine hydrochloride;

2-(3,4-diethoxyphenethyl)-5(2,2-di-n-butyl-1,3-benzoxathiol-5-yl)hydroxymethylpyrrolidine hydrochloride;

2-(3,4-methylenedioxyphenethyl)-5-(2,2-di-n-butyl-1,3-benzoxathiol-5-yl)hydroxymethylpyrrolidine hydrochloride, or others.

C. Compounds named above are the exemplary compounds only illustrating the procedure of preparations of compounds with various $R_1$, $R_2$ and Y substituents and X chain. Other compounds wherein $R_1$ substituent is —H, lower alkyl or cycloalkyl than those illustrated above or wherein $R_2$ substituent is —H, lower alkyl or cycloalkyl than those illustrated above, and if $R_1$ and $R_2$ are not equivalent each may be in cis- or trans- position, and wherein X may be $CH_2$—$CH_2$, CH=CH, or C≡C, may be prepared similarly by following the procedure of Parts A. and B. of this Example.

Similarly, compounds substituted on Y with substituents other than those illustrated above, such as lower alkyls, $OR_3$, where $R_3$ is —H or lower alkyl, may be prepared by the following procedure of Parts A. and B. of this preparation. Y substituents can be in the ortho, meta or para position and when a is 2, they may differ or both may be the same.

EXAMPLE 2

A. Preparation of 2-(p-Methoxyphenethyl)-5-(2,2-Dimethyl-1,3-Benzoxathiol-S-Oxide-5-yl)-Hydroxymethylpyrrolidine Hydrochloride 1 g of 2-p-methoxyphenethyl-5-(2,2-dimethyl-1,3-benzoxathiole)hydroxymethylpyrrolidine hydrochloride, was dissolved in methanol and the solution cooled in ice and treated with 0.85 g of m-chloroperbenzoic acid. The mixture was allowed to warm to room temperature and after 15 minutes evaporated to dryness. The residue was triturated with ethyl acetate and the solid material isolated by filtration and recrystallized from ethanol to yield 2(-p-methoxyphenethyl)-5-(2,2-dimethyl-1,3-benzoxathiol-S-oxide-5-yl)-hydroxymethylpyrrolidine hydrochloride, m.p. 222°–224° C.

B. Preparation of Other 2-(Substituted)-5-(2,2-Disubstituted-1,3-Benzoxathiol-S-Oxide-5-yl)-Hydroxymethylpyrrolidine Hydrochlorides Other compounds prepared in Example 1, Sections B. and C. can be similarly converted to their respective sulfoxides by following procedure of Example 2.A. hereinabove.

EXAMPLE 3

A. Preparation of 2(p-Methoxyphenethyl)-5-(2,2-Spirocyclopentane-1,3-Benzoxathiol-5-yl)Hydroxymethylpyrrolidine Hydrochloride 3 g of 5-(1,5-dioxo-2-aminoformyl-7-(p-methoxyphenyl)-2,2-spirocyclopentane-1,3-benzoxathiole heptane obtained in Preparation 15.A. was dissolved in 10 ml of methanol, and 10 ml of concentrated hydrochloric acid was added. The solution was stirred for 24 hours at room temperature, then evaporated to yield an oily residue. The residue was dissolved in 50 ml of methanol, the solution was cooled to about −40° C. with a dry ice acetone bath and treated with 300 mg of sodium borohydride. The solution was allowed to warm to room temperature and then evaporated. The residue was treated with ammonium chloride solution and ethyl acetate. The organic layer was separated, dried over potassium carbonate and evaporated to leave a residue which was dissolved in methanol. The mixture was acidified by cautious addition of a solution of hydrogen chloride in methanol. Evaporation of the solvent yielded an oil which was crystallized from acetonitrile-ethyl acetate to give 2 g of 2-p-methoxyphenethyl-5-(2,2-spirocyclopentane-1,3-benzoxathiol-5-yl)hydroxymethylpyrrolidine hydrochloride, m.p. 219°–220° C.

B. Preparation of Other 2-Substituted-Phenethyl-5-(2,2-Spirocycloalkane-1,3-Benzoxathiol-5-yl)HydroxymethylPyrrolidine Hydrochlorides Other cycloalkane benzoxathiole compounds are prepared similarly to the procedure of Example 3.A. but substituting 2,2-spirocyclopentane-5-(1,5-dioxo-2-aminoformyl-7-p-methoxyphenyl)heptyl-1,3-benzoxathiole with compounds prepared in Preparation 15.B. and 15.C.

EXAMPLE 4

A. Preparation of 2-(p-Methoxyphenethenyl)-5-(2,2-Dimethyl-1,3-Benzoxathiol-5-yl)HydroxymethylPyrrolidine Hydrochloride ($R_1$ and $R_2$ are $CH_3$; X is Ch=CH; and Y is 4—$OCH_3$)

3.5 g of 2,2-dimethyl-5(1,5-dioxo-2-aminoformyl-7-p-methoxyphenyl)hept-6-enyl-1,3-benzoxathiole (IXX) (Preparation 9.A.) was dissolved in 50 ml of methanol-concentrated aqueous hydrochloric acid (4:1). After 24 hours at room temperature the solution was evaporated to yield a residue consisting mainly of the intermediate iminium salt. The residue was dissolved in ethanol and the solution was cooled to about −40° C. The stirred solution was treated with approximately 200 mg of sodium borohydride and allowed to warm to room temperature. The mixture was evaporated to dryness and the residue stirred for 10 min. with a solution of 10% ammonium chloride in ethyl acetate. The organic layer was separated, dried with potassium carbonate and evaporated to yield a solid which was stirred with boiling methanol. The mixture was acidified by the addition of methanolic HCl, then cooled and filtered to yield 2.0 g of 2-(p-methoxyphenethenyl)-5-(2,2-dimethyl-1,3-benzoxathiol-5-yl)hydroxymethylpyrrolidine hydrochloride, m.p. 234° C.

B. Preparation of Other 2-(Substituted-Phenethenyl)-5-(2,2-Disubstituted-1,3-Benzoxathiol-5-yl)Hydroxymethylpyrrolidines Hydrochlorides Other alkene benzoxathiole compounds are prepared similarly to the procedure of Example 5.A. but substituting compound (XV) 2,2-dimethyl-5(1,5-dioxo-2-aminoformyl-7-p-methoxyphenethyl)hept-6-en-1-yl-1,3-benzoxathiole (IXX) with other compounds prepared in Preparation 9.B.

EXAMPLE 5

Conversion of Free Base to Salt

A. Preparation of 2-(p-Methoxyphenethyl)-5-(2,2-Dimethyl-1,3-Benzoxathiol-5-yl)Hydroxymethyl Pyrrolidine Hydrochloride Excess 3% hydrogen chloride in methanol is added to a solution of 1.0 g 2-(p-methoxyphenethyl)-5-(2,2-dimethyl-1,3-benzoxathiol-5-yl)hydroxymethylpyrrolidine in 20 ml of methanol. Diethyl ether is added until precipitation is complete. 2-(p-methoxyphenethyl)-5-(2,2-dimethyl-1,3-benzoxathiol-5-yl)hydroxymethylpyrrolidine hydrochloride is filtered, washed with ether, air dried and recrystallized.

B. Conversion of Other Free Bases to Salts

In a similar manner, all compounds of this invention in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 6

Conversion of Salt to Free Base

A. Preparation of 2-(p-Methoxyphenethyl)-5-(2,2-Dimethyl-1,3-Benzoxathiol-5-yl)HydroxymethylPyrrolidine 1.0 g of 2-p-methoxyphenethyl-5-(2,2-dimethyl-1,3-benzoxathiole hydroxymethyl)pyrrolidine hydrochloride is dissolved in 50 ml of water. A solution of sodium bicarbonate is added, and the pH adjusted to about pH 5. The resulting free base is extracted with ethyl acetate, the organic layer is then separated, washed twice with water, dried over magnesium sulfate and evaporated to yield 2-(p-methoxyphenethyl)-5-(2,2-dimethyl-1,3-benzoxathiol-5-yl)hydroxymethylpyrrolidine as the free base.

B. Conversion of Other Salts to Free Base

In a similar manner, all compounds of this invention in acid addition salt form may be converted to a free base.

EXAMPLE 7

Direct Interchange of Acid Addition Salts

A. 2-(p-methoxyphenethyl)-5-(2,2-dimethyl-1,3-benzoxathiol-5-yl)hydroxymethylpyrrolidine acetate prepared according to Example 6.B. (1.0 g) is dissolved in a solution of 1 ml 50% aqueous sulfuric acid in 10 ml ethanol and the resulting precipitate harvested. The product is suspended in ethanol and filtered, air dried, and recrystallized from methanol/acetone to yield 2-(p-methoxyphenethyl)-5-(2,2-dimethyl-1,3-benzoxathiol-5-yl)hydroxymethylpyrrolidine bisulfate.

B. In a similar manner, all compounds of this invention in acid adition salt form may be interchanged to another salt.

In Examples 8 through 13, the active ingredient is 2-(p-methoxyphenethyl)-5-(2,2-dimethyl-1,3-benzoxathiol-5-yl)hydroxymethylpyrrolidine hydrochloride. Other compounds of this invention and the pharmaceutically acceptable acid addition salts thereof may be substituted therein.

EXAMPLE 8

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 9

| Ingredients | Quantity per tablet, mgs. |
| --- | --- |
| Active ingredient | 100 |
| lactose, spray-dried | 148 |
| magnesium stearate | 2 |

The above ingredients are mixed and intorduced into a hard-shell gelatin capsule.

EXAMPLE 10

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE 11

| Ingredients | Quantity per tablet, mgs. |
| --- | --- |
| Active ingredient | 108 |

| Ingredients | Quantity per tablet, mgs. |
|---|---|
| lactose | 15 |
| cornstarch | 25 |
| magnesium stearate | 2 |

The above ingredients are mixed and introduced into a hard-shell gelatin capsule.

EXAMPLE 12

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 13

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |

What is claimed is:

1. A compound of the formula

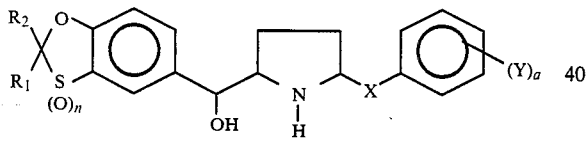

and the pharmaceutically acceptable, nontoxic, acid addition salts thereof, wherein R$_1$ and R$_2$ are each independently —H, lower alkyl, or cycloalkyl of 4–7 carbons, with the proviso that R$_1$ and R$_2$ cannot both be —H or cycloalkyl at the same time;

R$_1$ and R$_2$ taken together are cycloalkyl of 4–7 carbons;

n is 0 or 1;

X is (CH$_2$)$_2$, CH=CH, or C≡C;

Y is independently selected from the group of —H, —Fl, —Br, —Cl, lower alkyl, and —OR$_3$; wherein R$_3$ is —H or lower alkyl; and a is 1 or 2, or two Y's taken together are —OCH$_2$O—.

2. The compound of claim 1 and the pharmaceutically acceptable, nontoxic, acid addition salts thereof, wherein X is (CH$_2$)$_2$.

3. The compound of claim 2 wherein Y is lower alkyl or OR$_3$.

4. The compound of claim 3 wherein Y is OR$_3$.

5. The compound of claim 4 wherein R$_3$ is methyl.

6. The compound of claim 5 wherein n is 0 and a is 1.

7. The compound of claim 6 wherein R$_1$ and R$_2$ are each methyl, namely 2-p-methoxyphenethyl-5-(2,2-dimethyl-1,3-benzoxathiole-5-yl)hydroxymethylpyrrolidine and the pharmaceutically acceptable, nontoxic, acid addition salts thereof.

8. The compound of claim 3 wherein a is 2 and the two Y's are —OCH$_2$O— at the 3,4-positions.

9. The compound of claim 8 wherein n is O.

10. The compound of claim 9 wherein each R$_1$ and R$_2$ is methyl, namely 2-(3,4-methylenedioxyphenyl)ethyl-5-(2,2-dimethyl-1,3-benzoxathiol-5-yl)hydroxymethylpyrrolidine and the pharmaceutically acceptable, nontoxic, acid addition salts thereof.

11. The compound of claim 3 wherein R$_1$ and R$_2$ together is cycloalkyl of 4–7 carbons.

12. The compound of claim 11 wherein Y is hydrogen.

13. The compound of claim 11 wherein a is 1, Y is p-methoxy, and R$_1$ and R$_2$ taken together are cyclopentane, namely 2-(p-methoxyphenethyl)-5-(2,2-spirocyclopentane-1,3-benzoxathiol-5-yl)hydroxymethylpyrrolidine and the pharmaceutically acceptable, nontoxic, acid addition salts thereof.

14. The compound of claim 3 wherein n is 1.

15. The compound of claim 14 wherein Y is OR$_3$.

16. The compound of claim 15 wherein a is 1, R$_1$, R$_2$ and R$_3$ are each methyl, namely 2-p-methoxyphenethyl-5-(2,2-dimethyl-1,3-benzoxathiol-5-yl-S-oxide)hydroxymethylpyrrolidine and the pharmaceutically acceptable, non-toxic, acid addition salts thereof.

17. The compound of claim 1 wherein X is CH=CH.

18. The compound of claim 17 wherein Y is OR$_3$.

19. The compound of claim 18 wherein n is O.

20. The compound of claim 19 wherein a is 1, R$_1$, R$_2$ and R$_3$ are each methyl, namely 2-p-methoxyphenethyl-5-(2,2-dimethyl-1,3-benzoxathiol-5-yl)hydroxymethylpyrrolidine and the pharmaceutically acceptable, nontoxic, acid addition salts thereof.

21. The compound of claim 19 wherein R$_1$ and R$_2$ taken together are cycloalkyl of 4–7 carbons.

22. The compound of claim 18 wherein n is 1.

23. A pharmaceutically composition useful for the management of hypertension in human beings which composition comprises a therapeutically effective amount of a compound of claim 1 in admixture with a pharmaceutically acceptable excipient.

24. A method for management of hypertension in mammals which method comprises administering to a subject in need of such treatment a therapeutically effective amount of the compound of claim 1.

* * * * *